US007550567B2

(12) United States Patent
Metzner et al.

(10) Patent No.: US 7,550,567 B2
(45) Date of Patent: Jun. 23, 2009

(54) FIBRINOGEN PURIFICATION

(75) Inventors: Hubert Metzner, Marburg (DE); Uwe Liebing, Coelbe (DE); Annette Feussner, Marburg (DE); Joerg Lemmer, Ebsdorfergrund (DE); Stefan Schulte, Marburg (DE); Volker Gawantka, Lahntal (DE)

(73) Assignee: CSL Behring GmbH, Marburg (DE)

( * ) Notice: Subject to any disclaimer, the term of this patent is extended or adjusted under 35 U.S.C. 154(b) by 368 days.

(21) Appl. No.: 11/062,432

(22) Filed: Feb. 23, 2005

(65) Prior Publication Data
US 2005/0197493 A1 Sep. 8, 2005

(30) Foreign Application Priority Data
Feb. 24, 2004 (DE) ........................ 10 2004 009 400

(51) Int. Cl.
*C07K 14/75* (2006.01)
*C07K 1/16* (2006.01)
(52) U.S. Cl. ........................ 530/382; 530/412; 530/415; 530/416; 530/417
(58) Field of Classification Search ................ 530/382, 530/412, 415, 416, 417
See application file for complete search history.

(56) References Cited

U.S. PATENT DOCUMENTS

| | | | |
|---|---|---|---|
| 4,096,136 | A | 6/1978 | Ayers et al. |
| 4,170,590 | A | 10/1979 | Stephan et al. |
| 4,188,318 | A | 2/1980 | Shanbrom |
| 4,210,580 | A | 7/1980 | Amrani |
| 4,272,523 | A | 6/1981 | Kotitschke et al. |
| 4,960,757 | A | 10/1990 | Kumpe et al. |
| 5,043,428 | A | 8/1991 | Heimburger et al. |
| 5,099,003 | A | 3/1992 | Kotitschke et al. |
| 5,252,709 | A | 10/1993 | Burnouf et al. |
| 5,723,579 | A | 3/1998 | Buettner et al. |
| 5,773,033 | A | 6/1998 | Cochrum et al. |
| 5,783,663 | A | 7/1998 | Mondorf et al. |
| 5,834,420 | A | 11/1998 | Laub et al. |
| 6,037,457 | A | 3/2000 | Lord |
| 6,239,261 | B1 | 5/2001 | Heimburger et al. |
| 6,582,603 | B1 | 6/2003 | Suzuki et al. |
| 6,740,736 | B2 * | 5/2004 | McCreath ............. 530/382 |
| 6,960,463 | B2 * | 11/2005 | Kanellos et al. ........ 435/226 |

FOREIGN PATENT DOCUMENTS

| | | |
|---|---|---|
| EP | 0 366 946 B1 | 5/1990 |
| EP | 0 408 029 B1 | 1/1991 |
| EP | 0 789 030 A1 | 8/1997 |
| GB | 1 551 928 | 9/1979 |
| WO | WO 89/12065 A1 | 12/1989 |
| WO | WO 90/12803 | 11/1990 |
| WO | WO 93/05067 | 3/1993 |
| WO | WO 95/25748 | 9/1995 |
| WO | WO 99/05176 | 2/1999 |
| WO | WO 99/37680 | 7/1999 |
| WO | WO 99/51724 | 10/1999 |
| WO | WO 00/17234 | 3/2000 |
| WO | WO 00/17239 | 3/2000 |
| WO | WO 01/27623 A2 | 4/2001 |
| WO | WO 01/48016 A1 | 7/2001 |
| WO | WO 2004/007533 A1 | 1/2004 |

OTHER PUBLICATIONS

Vukovich, T. (Proceedings of the Serono Symposia (1979), Volume Date 1977, 15[Haemostasis Thromb.], 407-10).*
Goheen et al., "Protein Losses in Ion-Exchange and Hydrophobic Interaction High-Performance Liquid Chromatography," *Journal of Chromatography A* 890:73-80 (2000).
Jennissen, "Critical Hydrophobicity HIC," Derwent Abstract XP002342368 (2003).
European Search Report for EP 05 003017, Sep. 15, 2005.
Blombäck et al., "Purification of Human and Bovine Fibrinogen," *Arkiv För Kemi* 10:415-443 (1956).
Dempfle et al., "Purification of Human Plasma Fibrinogen by Chromatography on Protamine-Agarose," *Thrombosis Research* 46:19-27 (1987).
Deutsch et al., "Plasminogen: Purification from Human Plasma by Affinity Chromatography," *Science*, 170:1095-1096 (1970).
Jakobsen et al., "A Modified Beta-Alanine Precipitation Procedure to Prepare Fibrinogen Free of Antithrombin-III and Plasminogen," *Thrombosis Research* 3:145-159 (1973).
Martinowitz et al., "Fibrin Tissue Adhesives," *Thrombosis and Haemostasis*, 78:661-666, (1997).
Matsuda et al., "A Simple, Large Scale Method for Preparation of Plasminogen-Free Fibrinogen," *Thrombosis Research* 1:619-630 (1972).
Radosevich et al.; "Fibrin Sealant: Scientific Rationale, Production Methods, Properties, and Current Clinical Use," *Vox Sanguinis*, 72:133-143 (1997).
Schlag et al., "Epileptic Seizures Following Cortical Application of Fibrin Sealants Containing Tranexamic Acid in Rats," *Acta Neurochirurgica*, 144:63-69 (2002).

(Continued)

*Primary Examiner*—David Lukton
(74) *Attorney, Agent, or Firm*—Finnegan, Henderson, Farabow, Garrett & Dunner, L.L.P.

(57) ABSTRACT

The present invention relates to a process for purifying fibrinogen, which comprises one or more process steps in which one or more contaminating proteins are depleted by negative chromatography and/or negative adsorption using cation exchanger, hydrophobic gel and/or dye gel. In addition, the invention relates to the fibrinogen which is obtained by the process of the invention and which is notable for improved stability, and to the production and use of pharmaceutical preparations comprising this fibrinogen.

21 Claims, 2 Drawing Sheets

OTHER PUBLICATIONS

Scott et al., "Human Factor XIa Cleaves Fibrinogen: Effects on Structure and Function," *Archives of Biochemistry and Biophysics*, 249(2):480-488 (1986).

Sierra, "Fibrin Sealant Adhesive Systems: A Review of Their Chemistry, Material Properties and Clinical Applications," *Journal of Biomaterials Applications*, 7:309-352 (1993).

Suzuki et al., "A Simple Technique for Purification of Fibrinogen from Plasma by Affinity Chromatography on Ristocetin-Agarose," *Thrombosis Research* 18:707-715 (1980).

Takeda, "Studies of the Metabolism and Distribution of Fibrinogen in Healthy Men with Autologous $^{125}$I-labeled Fibrinogen," *Journal of Clinical Investigation* 45(1):103-111 (1966).

Vila et al., "A Rapid Method for Isolation of Fibrinogen from Human Plasma by Precipitation with Polyethylene Glycol 6,000," *Thrombosis Research* 39:651-656 (1985).

Vuento et al., "Purification of Fibronectin from Human Plasma by Affinity Chromatography Under Non-Denaturing Conditions," *Biochem. J.* 183:331-337 (1979).

Derwent Abstract of WO 91/01808.

Derwent Abstract of EP 555135A.

English abstract of Kotitschke et al. (DE 29 03 131 A1, published Aug. 1979).

English abstract of Dazey et al. (EP 0 555 135 B1, published Aug. 1993).

English abstract of Seidel et al. (WO 91/01808, published Feb. 1991).

\* cited by examiner

Figures
Figure 1a: SEC-HPLC of sample purified via HIC prior to storage (655-11-109W)
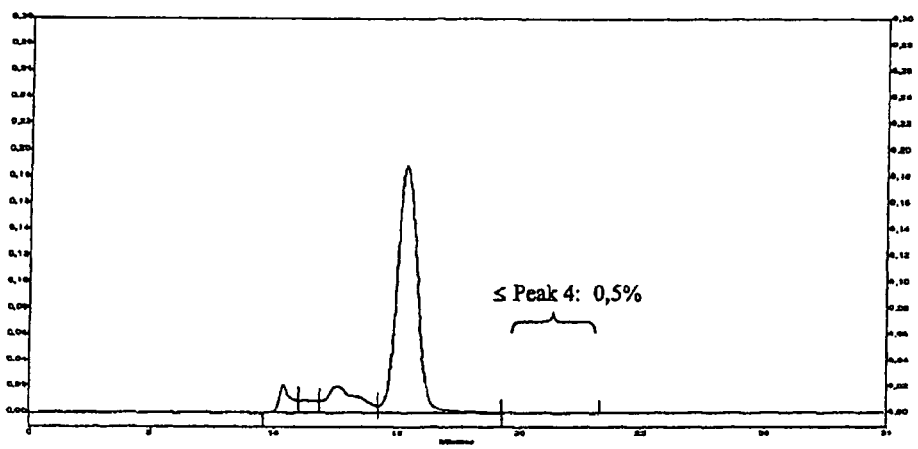
Figure 1b: SEC-HPLC of sample purified via HIC after storage of 2 months at 30°C (655-11-109W (t=2 mon/30°C))
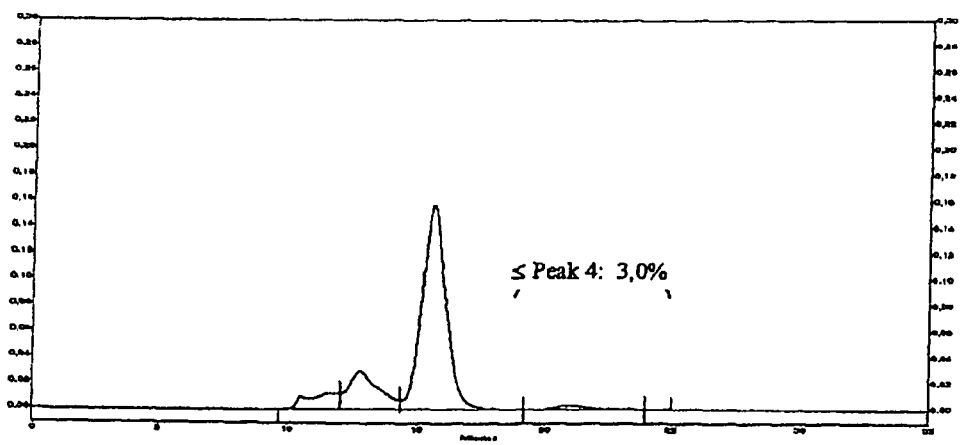

Figure 1c: SEC-HPLC of sample purified via HIC after storage of 2 months at 30°C (655-11-075W3 (t=2 mon/30°C))
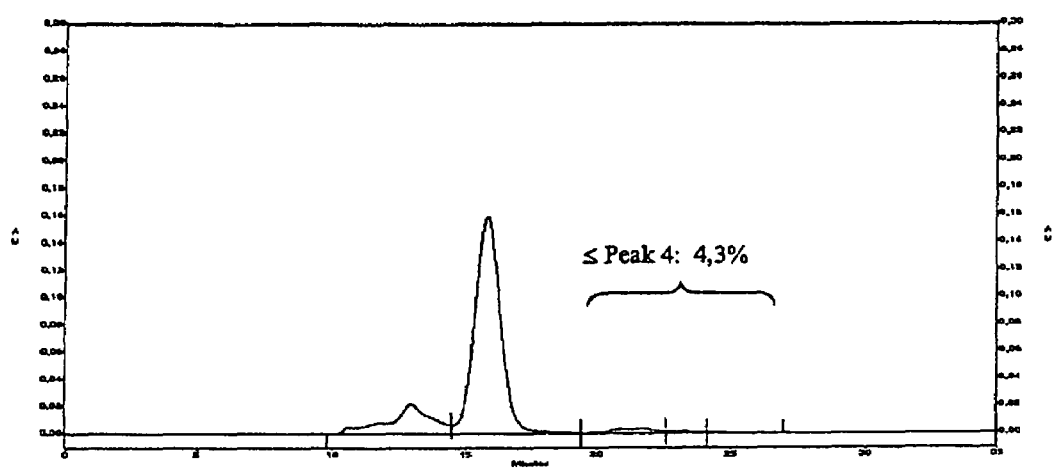

FIBRINOGEN PURIFICATION

This application claims priority to German application 102004669400.0, filed Feb. 24, 2004.

The present invention relates to a process for purifying fibrinogen, which comprises one or more process steps in which one or more contaminating proteins are depleted by negative chromatography and/or negative adsorption using cation exchanger, hydrophobic gel and/or dye gel. In addition, the invention relates to the fibrinogen which is obtained by the process of the invention and which is notable for improved stability, and to the production and use of pharmaceutical preparations comprising this fibrinogen.

Fibrinogen plays a key part in the coagulation of blood. Blood vessels are almost always damaged in the event of injuries or operations, and hemorrhages occur. The coagulation of blood causes the blood to solidify in the region of minor wounds, and the bleeding ceases. The coagulation system thus protects the body from large blood losses. In the coagulation of blood, the soluble fibrinogen present in the blood plasma is converted in the presence of thrombin to the fibrous insoluble fibrin. If fibrinogen is lacking, the coagulation of blood does not function correctly. The deficiency can be compensated by administering fibrinogen isolated from, for example, human blood plasma. Because of its importance for hemostasis and wound healing, fibrinogen has great importance in clinical use.

Because of this great clinical importance of fibrinogen, the literature contains diverse references concerned with various methods for purifying this important protein. Fibrinogen is mainly purified from human, and more rarely also from animal, plasma. It is likewise possible to purify recombinant fibrinogen, e.g. from cell culture after recombinant expression, or from the milk of transgenic animals.

Human plasma contains a complex mixture of more than 100 proteins, with fibrinogen accounting for about 2% of the total amount of protein. The purification and isolation of fibrinogen therefore usually requires a plurality of steps and diverse combinations are possible for these individual process steps.

One important component of the purification of fibrinogen from human plasma is conventionally precipitation. Known precipitation methods use amino acids such as glycine or alanine, see, for example, EP 0 383 234, WO 01/48016 or Jakobsen & Kierulf (Thrombosis Research 3 (1973) 145-159), ammonium sulfate, see, for example, U.S. Pat. No. 5,773,033, U.S. Pat. No. 6,037,457 or Takeda (Journal of Clinical Investigation 45 (1966) 103-111), polymers such as, for example, polyethylene glycol (PEG), see, for example, WO 95/25748 or Vila et al. (Thrombosis Research 39 (1985) 651-656), ethanol, see, for example, EP 0 408 029, where fibrinogen is precipitated and separated from other plasma proteins with 5-10% ethanol, or U.S. Pat. No. 5,099,003 or Blombäck & Blombäck (Arkiv För Kemi 10 (1956) 415-443), sulfated polysaccharides (SPS, e.g. heparin), see, for example, WO 99/37680 and U.S. Pat. No. 4,210,580 and solutions of low ionic strength, see, for example, U.S. Pat. No. 4,188,318 and DE 26 36 757.

The purity of fibrinogen obtained solely on the basis of precipitations is, however, not yet sufficient for some applications, so that various adsorption and chromatography steps are described in addition or alternatively for purifying fibrinogen in the prior art.

Anion exchange chromatography is frequently used in the area of ion exchange chromatography. Reference may be made in this connection to EP 0 555 135, in which fibrinogen is bound in a main process step to an anion exchanger column while albumin and inactivators for example do not bind. Fibrinogen is subsequently eluted from the column. In WO 93/05067, the binding of fibrinogen to anion exchanger is used to remove again the detergents added for virus inactivation. WO 01/48016 describes the binding of fibrinogen to ion exchange material preferably using ω-amino acids which delay fibrinogen degradation, such as, for example, ε-aminocaproic acid (EACA), in the loading and/or washing buffer. Such a process step makes it possible in particular to deplete efficiently the contaminating plasminogen from fibrinogen-containing solutions.

Cation exchanger chromatography is used for example in the purification of fibrinogen from the milk of transgenic animals as described in WO 00/17234. The conditions chosen in this case also result in binding of fibrinogen to the column material, and thus make it possible to remove for example casein.

The property of fibrinogen binding to cation exchanger is utilized in WO 91/01808 in order to remove fibrinogen, lipoproteins and urea selectively from fluids such as, for example, blood.

In WO 89/12065, fibrinogen is purified in one process step by a heparin-Sepharose column. The conditions are chosen so that fibrinogen is adsorbed onto the column material and, in particular, albumins, immunoglobulins and virus-inactivating substances can be removed.

The possibility of purifying fibrinogen by hydrophobic interactions is also described. In WO 00/17239, fibrinogen is purified from the milk of transgenic animals in one process step by binding to a hydrophobic column in the presence of salts with subsequent elution. The possibility of using a hydrophobic column for fibrinogen from human plasma is likewise mentioned.

Various affinity chromatographies having different ligands able to bind fibrinogen selectively are also described. Reference may be made in this connection for example to U.S. Pat. No. 6,037,457 or WO 99/05176, which describe antibodies which specifically bind fibrinogen or fibrinogen peptides and can be employed inter alia for purifying fibrinogen. EP 0 789 030, U.S. Pat. No. 5,723,579 and U.S. Pat. No. 5,783,663 describe peptides which bind fibrinogen and correspondingly can be used as ligands in affinity columns for purifying fibrinogen. Immobilized ristocetin has likewise been employed for binding fibrinogen, and the latter was eluted again with 8 M urea (Suzuki et al., Thrombosis Research 18 (1980) 707-715). In WO 99/20655, finally, inactivated thrombin is used as ligand for thrombin substrates, which include fibrinogen. WO 90/12803 describes so-called IMAC (immobilized metal affinity chromatography) for purifying certain proteins. Human fibrinogen is also mentioned as possible protein binding to the metal chelate matrix. Fibrinogen also binds to protamine-agarose and can subsequently be eluted at acidic pH, see, for example, U.S. Pat. No. 6,037,457 or Dempfle & Heene (Thrombosis Research 46 (1987) 19-27).

It is common to all these processes or process steps mentioned that the conditions are chosen so that fibrinogen binds to the chromatography or adsorption material and must subsequently be detached again from the gel material.

Processes in which fibrinogen passes through the column have to date been described only for processes in which it is desired to fractionate the starting material into various "useful fractions" or in which fibrinogen is an impurity.

Plasma or cryoprecipitate contains besides fibrinogen also large amounts of other clinically significant plasma proteins, so that it is also used as starting material for the fractionation and isolation of factor VIII (F VIII), fibronectin and von Willebrand factor. For this reason, chromatographic process steps able to separate all four or at least two of the main proteins are also used. For this purpose, anion exchangers are used under conditions which do not bind fibrinogen but do, for example, F VIII, von Willebrand factor and fibronectin, which are subsequently eluted selectively by different ionic strengths. Reference may be made in this connection for example to WO 89/12065, EP 0 359 593 or U.S. Pat. No. 5,252,709. The conditions chosen in EP 0 383 234 for the anion exchanger are such that only F VIII binds, whereas von Willebrand factor, fibronectin and fibrinogen pass through the column or remain in the supernatant (batch process). EP 0 408 029 and U.S. Pat. No. 5,138,034 finally include inter alia a fractionation process in which initially F VIII and fibronectin are removed by precipitation through a freeze/thaw treatment, factor IX (F IX) is adsorbed onto a subsequent anion exchanger column, and the fibrinogen is precipitated from the flow-through of the column with ethanol. The aim in all these cases is to separate the clinically significant main proteins, which can then be subjected singly to further purification steps before their pharmaceutical use. A similar process step with an anion exchanger column is also used as possible intermediate step in the purification of fibrinogen to remove F VIII in EP 0 555 135. In one embodiment in WO 96/02571 or U.S. Pat. No. 5,834,420, ion exchanger material similar to WO 89/12065 is employed to remove F VIII and von Willebrand factor to purify fibrinogen. Proteins such as F VIII and von Willebrand factor have, however, no effect on the stability of fibrinogen. This process step is often also used to prepare F VIII concentrates in order to free them as completely as possible from contaminants such as, for example, immunoglobulins, fibronectin and fibrinogen. Reference may be made in this connection for example to U.S. Pat. No. 5,043,428 and EP 0 173 242. U.S. Pat. No. 4,210,580 describes a process for purifying fibronectin in which fibrinogen can be removed after the heparin precipitation by washing a subsequent anion exchanger column. U.S. Pat. No. 5,099,003 also makes use of an anion exchanger, but in this case to remove factors II, VII, IX and X, which would otherwise cause gelation and clumping of the fibrinogen-containing solution after a virus-inactivating treatment with β-propiolactone and UV irradiation. DE 29 02 158, which describes processes for preparing fibrinogen, prothrombin complex, antithrombin III and a solution of storage-stable serum proteins, describes inter alia a variant in which initially the prothrombin complex (F II, F VII, F IX and F X) is obtained by adsorption on anion exchangers, and subsequently fibrinogen is also isolated from the flow-through by adsorption with colloidal silica. However, since fibrinolysis occurs frequently during this purification sequence and has an adverse effect on the isolation of fibrinogen, the preferred variant is first to remove fibrinogen by adsorption onto silica and subsequently to isolate the prothrombin complex with the aid of anion exchangers. In this case therefore the use of an anion exchanger tends to have a disadvantageous effect on the quality of the fibrinogen which is to be isolated at the same time from the flow-through.

Finally, WO 99/51724 describes a "negative" chromatographic process for purifying heterologous proteins, including fibrinogen, from the milk of transgenic animals. However, in this case, hydroxyapatite is used as gel material in order to bind contaminating milk proteins.

There are also descriptions of specific negative affinity chromatographies such as, for example, immobilized gelatin able to deplete fibronectin through specific binding (see, for example, Vuento & Vaheri, Biochem. J. (1979) 183, 331-337). However, fibronectin is a structural protein which has no effect on the stability of fibrinogen.

The ability of lysine or analogous compounds to bind plasminogen very specifically, and the possibility of utilizing this ability for purifying plasminogen via an affinity chromatography with L-lysine-substituted Sepharose is also described (Deutsch & Mertz, Science 170 (1970) 1095-1096; Matsuda et al., Thrombosis Research 1 (1972) 619-630). This ability of lysine ligands is utilized in some fibrinogen purification processes as process step in order to deplete contaminating plasminogen. Reference may be made in this connection for example to WO 95/25748 or WO 93/05067. However, in this case there is very specific depletion of only one protein, plasminogen, because the lysine binds very specifically to a particular epitope (kring domains) of plasminogen.

WO 01/27623 describes a process allowing isoagglutinins (blood group antibodies) to be removed from blood or blood constituents such as, for example, fibrinogen. In this case, antigens (e.g. oligosaccharides) are used as ligands which are able to bind isoagglutinins specifically in an affinity column. Removal of isoagglutinins is advantageous to avoid complications when the blood groups of the donated blood or of the donated blood components differ from the recipient's blood group. Isoagglutinins have no effect on the stability of fibrinogen to proteolysis.

EP 0 366 946 and U.S. Pat. No. 5,094,960 which describe a process for removing lipid-soluble process chemicals from biological material such as, for example, plasma, cryo-precipitate, coagulation factors and fibrinogen are also used. In this case, a hydrophobic chromatography column which adsorbs the process chemicals but not the proteins of the biological material under the chosen conditions is used. The aim of this process is merely to remove chemical substances which were added for example to inactivate viruses. Proteins such as, for example, coagulation factors, which include inter alia fibrinogen-degrading factors such as factor XI (F XI) (Scott et al., Arch Biochem Biophys 249 (1986) 480-488) are not intended to bind under the chosen conditions and are not intended in this patent to be depleted. Similarly, the intention in DE 29 03 131 is merely to exchange ions through the use of ion exchanger material. This patent describes a process for the simultaneous purification of four products (antihemophilic globulin A, prothrombin complex, solution of storage-stable serum proteins and fibrinogen), in which case a plasma from which calcium ions have been removed, and on use of citrated plasma additionally citrate ions have been removed, is required as starting material. In this case, cation exchangers replace the calcium ions by sodium or hydrogen ions and anion exchangers replace the citrate ions by chloride or hydroxide ions. It is then possible to isolate from the ion exchanger plasma obtained in this way inter alia fibrinogen by adsorption onto silica. The cation exchanger used in this case however merely serves to replace calcium ions in order to avoid initiating a coagulation response; no purification takes place by this step.

Adsorptions are likewise employed in the purification of plasma proteins. Thus, DE 29 03 131 makes use of a tricalcium phosphate (TCP) adsorption to purify the prothrombin complex. WO 95/25748 employs it to remove the prothrombin complex as one process step for purifying fibrinogen. Mention should also be made of the adsorption using aluminum hydroxide ($Al(OH)_3$), which binds factors of the prothrombin complex and may also play a part for example in the removal of lipids. $Al(OH)_3$ is used for example in EP 0 383 234 or WO 01/48016. Mention should also be made in this connection of a possible use of barium sulfate ($BaSO_4$).

It is common to all the described processes for negative chromatography/adsorption, with the exception of EP 0 366 946 or U.S. Pat. No. 5,094,960, in which only process chemicals are removed, and DE 29 03 131, in which only calcium and citrate ions are removed, that there is use of gel materials other than those described for the process step(s) of the invention. An additional point is that the particular advantage of the process step of the invention is that it is possible by efficient depletion of one or more contaminating proteins, especially fibrinogen-degrading proteins or their precursors, to obtain a fibrinogen preparation whose stability in solution is significantly increased. For industrial isolation it is of particular interest to develop a purification process which not only can be carried out economically from the industrial viewpoint but also leads to a fibrinogen which remains very substantially stable on prolonged storage in solution.

Fibrinogen is a very large protein with a complex structure. It is a glycoprotein of about 340 kDa consisting of two symmetrical halves. Pairs of alpha (Aα), beta (Bβ) and gamma (γ) chains form an elongate molecular structure (about 47 nm) which forms three domains (a central E domain and two identical D domains). This complex structure is indispensable for efficient formation of a stable fibrin matrix. The alpha chain in particular is affected by incipient proteolytic degradation by fibrinogen-degrading proteases. Damage of this type to the alpha chain results, after the action of thrombin, in a delayed start of coagulation and suggests that proteolysis of the alpha chain(s) may influence fibrin polymerization. The three-dimensional structure of the fibrin clot is also influenced by a damaged alpha chain. The fibrin network is finer and has thinner fibrils and less mechanical stability. The C-terminal ends of the alpha chains comprise amino acid sequences on which linkages between adjacent fibrin molecules, catalyzed by activated F XIII, are based. Missing crosslinks reduce the stability of the fibrin matrix. All this shows that fibrinogen with seriously damaged alpha chains has reduced quality and is undesirable for pharmaceutical use for example in fibrin glues. Comparable statements also apply to the proteolytic degradation of the other fibrinogen chains, but this usually takes place with slower kinetics. The advantage of the process steps of the invention is the depletion of fibrinogen-degrading proteins with the result of increased stability of the fibrinogen in aqueous solution.

Processes which maximize the removal of fibrinogen-degrading proteins and proenzymes thereof are therefore particularly advantageous, because the stability and efficacy of the resulting fibrinogen solution is decisively improved even on prolonged storage in liquid form. Storage in liquid form is particularly advantageous for fibrinogen because immediate use of the active substance on the patient is possible and thus more time is spent in reconstituting lyophilized preparations or thawing and warming frozen preparations. However, even if stored as lyophilizate or in the frozen state, it is advantageous for the reconstituted or thawed fibrinogen to be stable for longer. This is evident for example in situations where material has been reconstituted as a precaution for example for operations, but use was then unnecessary on the basis of medical considerations. This material must be discarded if the stability is only short-term and could no longer be used at a later time. On use of fibrin glues it is particularly advantageous for fibrinogen to be in liquid form. The commercially available glues mostly comprise two components. One component comprises fibrinogen, frequently together with factor XIII and a fibrinolysis inhibitor such as aprotinin, and the other component comprises thrombin, frequently together with calcium ions. Reconstitution in order to make the glue ready for use requires a relatively long time, especially since fibrinogen is present in high concentrations.

A further great advantage of the fibrinogen isolated by the process of the invention is the possibility of storage as liquid for a certain time even at room temperature, thus possibly improving for example the use properties in emergency situations. It is also advantageous on lengthy transport routes where low temperatures may, where appropriate, not be ensured throughout, if the stability can be ensured even at room temperature during this period. Stable storage of fibrinogen in solution thus facilitates in many respects the production, usage, transport and administration to the patient. Owing to the advantageously increased stability of fibrinogen produced by the process of the invention it is additionally possible in many pharmaceutical preparations to dispense with the addition of fibrinolysis or fibrinogenolysis inhibitors which may, in some circumstances, lead to unwanted side effects or which should be avoided to reduce potential risks.

In summary, therefore, despite the numerous purification methods described, there remains a need for improved methods which make economic production of stable fibrinogen solutions possible on the industrial scale.

The present invention is thus based on the object of indicating a process for purifying fibrinogen which provides a fibrinogen of high stability in a good yield. Surprisingly, purification processes which can also be carried out economically on the industrial scale and which lead to a fibrinogen whose stability in solution is significantly increased has been found.

The invention therefore relates to a process for purifying fibrinogen, which comprises one or more process steps in which one or more contaminating proteins are depleted by negative chromatography or chromatographies and/or negative adsorption(s) using organic cation exchanger, hydrophobic gel and/or dye gel. The invention further relates to a fibrinogen preparation which is obtainable by the described process steps and which is notable for improved stability after storage at room temperature and/or by a reduced content of fibrinogen-degrading proteases or proenzymes thereof.

The various dye gels proposed in this invention, which carry diverse dye ligands, are able to deplete various proteins, making it possible to produce a fibrinogen-containing solution with high stability of the fibrinogen.

The use of inorganic, slightly soluble salts such as TCP, $Ba(SO_4)$ and $Al(OH)_3$ does not, however, lead to a fibrinogen preparation of the invention. However, the gel materials of the invention can also be employed in combination with inorganic, slightly soluble salts such as TCP, $Ba(SO_4)$ and $Al(OH)_3$.

The proportion of low molecular weight fibrinogen degradation fragments on storage at 30° C. is regarded as a measure of the stability of fibrinogen. These degradation fragments are determined by size exclusion chromatography as peaks with a smaller molecular weight than the main fibrinogen peak (peak 4 or ≦peak 4). A fibrinogen preparation is regarded as stable within the meaning of the invention if the absolute proportion of fibrinogen degradation fragments (peak 4≦peak 4) on storage at 30° C. in the liquid state is less than 3%, more preferably less than 2.5%, after one month.

Purification within the meaning of the present invention may be a chromatographic purification process or a batch adsorption process.

Processes which have proved useful are those in which initially a fibrinogen preparation with a purity of at least 50% (w/w), more preferably at least 70% (w/w), is produced by one or more precipitation steps and is then further purified by negative chromatography or chromatographies and/or negative adsorption(s) using cation exchanger, hydrophobic gel and/or dye gel and, where appropriate, by additional, described processes.

Prior art processes differ fundamentally from the negative chromatography or negative adsorption process step of the invention, with which the conditions are chosen so that only a relatively small proportion or none of the fibrinogen binds and it thus passes through the column in the chromatographic separation. The predominant portion of fibrinogen is thus present in the flow-through or, in the case of adsorption, in the supernatant. The advantage of the process step of the invention is, inter alia, that it is possible to choose conditions which do not impair the structure and functionality of fibrinogen and, in addition, lead to high yields. Since it is necessary in the process step of the invention, especially after previous purification by precipitations, to bind and remove essentially only subsidiary components, cost-effective industrial implementation is possible owing to the small column dimensions and simple technical equipment. By a comparison therewith, the chromatographies/adsorptions with fibrinogen binding which have been described previously comprise some disadvantages. Since fibrinogen is bound, large column dimensions are necessary and make the process more costly owing to the large amounts of gel material and because of the more complex technical equipment. Elutions via, for example, salt gradients may also represent an impediment for industrial production. It is also necessary in some cases to employ harsh chemical conditions which may impair the functionality of fibrinogen in order to elute the bound fibrinogen again. In some cases also the described purifications are associated with large losses of fibrinogen or else cannot be employed economically for industrial purifications of fibrinogen, e.g. owing to costly or not commercially available gel materials.

The following embodiments have proved to be advantageous:

Process as described above using sulfomethyl groups (S types), sulfopropyl groups (SP types), carboxymethyl groups (CM types) or other suitable negatively charged functional groups as functional group of the cation exchanger.

Process as described in the foregoing, where the cation exchanger is Fractogel EMD $SO_3^-$ 650, Macro-Prep 50 S, CM-Sepharose CL-6B, Fractogel EMD CM-650, Fractogel TSK CM 650, Fractogel EMD CM, SP Sepharose, Heparin Fractogel and/or Heparin Sepharose CL 6B.

Process as described in the foregoing, where the hydrophobic gel comprises alkyl groups as functional groups.

Process as described in the foregoing, where the hydrophobic gel comprises phenyl groups or derivatized phenyl groups as functional groups.

Process as described in the foregoing, where the hydrophobic gel comprises propyl, butyl, pentyl, hexyl or octyl groups as functional groups.

Process as described in the foregoing, where the hydrophobic gel used is Macro Prep Methyl, Fractogel EMD Propyl 650, Fractogel EMD Butyl 650, Fractogel TSK Butyl 650, Macro Prep t Butyl, Butyl Cellufine, Butyl Sepharose 4 Fast Flow, Butyl S-Sepharose 6 Fast Flow, HIC-Fractogel Pentyl, Hexyl S-Sepharose 6 Fast Flow, Octyl Sepharose CL 4B, HIC-Fractogel HW 65 Propyltentakel, Fractogel HW 65 Butyltentakel, Fractogel TA 650, Phenyl Sepharose HP, Phenyl Sepharose Fast Flow, Phenylalanin Sepharose, Thiopropyl Sepharose 6B and/or Pyridyl S-Sepharose 6 Fast Flow.

Process as described in the foregoing, where a blue dye gel is used as dye gel.

Process as described in the foregoing, where a red or green dye gel is used as dye gel.

Process as described in the foregoing, where the dye gel is Blue Hyper D, Mimetic Blue Agarose, Mimetic Blue SA P6XL, Mimetic Blue 1 P6XL, Blue Trisacryl Plus LS, Blue Uniflow, Blue Sepharose 6FF, Blue Sepharose CL 6B, Red Sepharose CL 6B, Fractogel TSK AF Green and/or Matrex gel Green A.

Process as described in the foregoing, where a pH between 6 and 9 is used during the process step with negative chromatography and/or negative adsorption.

Process as described in the foregoing, where the process step with negative chromatography and/or negative adsorption is carried out at a temperature of 0-30° C.

Process as described in the foregoing, where the yield of fibrinogen in the flow-through of the negative chromatography or in the supernatant of the negative adsorption is $\geq 50\%$, preferably $\geq 70\%$.

Process as described in the foregoing, where the process step which includes the negative adsorption or chromatography is carried out in the presence of substances which weaken the binding of plasminogen to fibrinogen.

Process as described in the foregoing, where a mixture obtained from blood, milk from transgenic animals or a fermentation supernatant or a fraction produced therefrom is used as starting material.

Process as described in the foregoing, where human plasma, a plasma fraction or cryoprecipitate is used as starting material.

Process as described in the foregoing, where one or more process steps include an aluminum hydroxide treatment.

Process as described in the foregoing, comprising one or more process steps in which fibrinogen is precipitated.

Process as described in the foregoing, comprising one or more precipitations with glycine or other amino acids.

Process as described in the foregoing, comprising one or more process steps in which plasminogen is removed via gel material with lysine or lysine analogs as functional group.

Process as described in the foregoing, comprising one or more process steps for depletion and/or inactivation of infectious particles.

Process as described in the foregoing, where one process step is a pasteurization and/or UV irradiation and/or a nanofiltration.

Process as described in the foregoing, comprising one or more ultrafiltrations and/or dialyses.

Process as described in the foregoing, using filter materials with a molecular weight limit (cutoff) of from 100 to 500 kDa.

Process as described in the foregoing, comprising one or more sterilizing filtrations.

Process as described in the foregoing, combining the following process steps: preparation of a plasma fraction, adsorption onto aluminum hydroxide, inactivation of infectious particles such as, for example, viruses, precipitation, further purification and/or inactivation steps, negative chromatography and/or negative adsorption, ultrafiltration, sterilizing filtration.

Process as described in the foregoing, where the further purification step is a process step to remove plasminogen.

Process as described in the foregoing, where the sequence and/or the number of the individual process steps is altered.

Process as described in the foregoing, where one of the process steps of the invention is used, and the plasma proteins to be removed are eluted after carrying out the negative chromatography and/or the negative adsorption from the cation exchanger, hydrophobic gel and/or dye gel.

Process as described in the foregoing for isolating F XII, plasminogen, t-PA and/or F XI.

Fibrinogen preparation obtainable by one of the processes described in the foregoing.

F XII, plasminogen, t-PA and/or F XI which have been produced by one of the processes described in the foregoing.

Production of a pharmaceutical preparation which comprises a fibrinogen produced by one of the processes described in the foregoing.

Pharmaceutical preparation which comprises a fibrinogen produced by one of the processes described in the foregoing.

Pharmaceutical fibrinogen preparation wherein the F XI content is $\leq 1$, preferably $\leq 0.2$, ng per $OD_{280-320}$.

Pharmaceutical fibrinogen preparation wherein the F XII content is $\leq 20$, preferably $\leq 10$, ng per $OD_{280-320}$.

Pharmaceutical fibrinogen preparation wherein the t-PA content is $\leq 0.02$, preferably $\leq 0.01$, ng per $OD_{280-320}$.

Pharmaceutical preparation as described in the foregoing, where the absolute proportion of fibrinogen degradation fragments on storage at 30° C. in the liquid state is less than 3%, preferably less than 2.5%, after one month. Use of a pharmaceutical preparation after one of the processes described in the foregoing.

Use of a pharmaceutical preparation after one of the processes described in the foregoing as product for the treatment of fibrinogen deficiency states.

Use of a pharmaceutical preparation after one of the processes described in the foregoing as component of a fibrin glue.

Use of a pharmaceutical preparation after one of the processes described in the foregoing as component for producing a fibrin matrix.

Use of a pharmaceutical preparation after one of the processes described in the foregoing as component of a diagnostic aid.

Fibrinogen preparation according to one of the processes described in the foregoing as component of a multicomponent glue. Fibrinogen preparation according to one of the processes described in the foregoing, comprising the formulation ingredient arginine as component of a multicomponent glue. Fibrinogen preparation according to one of the processes described in the foregoing comprising the formulation ingredients NaCl, $Na_3$ citrate, Arg×HCl and $CaCl_2$ as component of a multi-component glue. Fibrinogen preparation according to one of the processes described in the foregoing, comprising the formulation ingredients NaCl (0-500 mM), $Na_3$ citrate (0-50 mM), Arg or Arg×HCl (0.05-2.0 mol/l) and $CaCl_2$ (0.1-5 mM) or mixtures thereof as component of a multicomponent glue. Fibrin glue which comprises a fibrinogen component according to one of the processes described in the foregoing, an F XIII component and a thrombin component as separate components.

Fibrin glue which comprises a fibrinogen component according to one of the processes described in the foregoing, to which F XIII is added, and a thrombin component as separate components.

Further embodiments relate to the subject-matter of the claims and further features and advantages of the invention are evident from the description of the preferred embodiments, and the examples and figures.

A BRIEF DESCRIPTION OF THE FIGURES FOLLOWS

FIG. 1 shows the investigation of fibrinogen-containing solutions for fibrinogen degradation fragments by SEC-HPLC. It is shown that the proportion of fibrinogen degradation fragments can be significantly reduced on storage at 30° C. for two months, and the stability of fibrinogen in solution is thus increased, through use of a negative hydrophobic interaction chromatography.

FIG. 1a: Fibrinogen-containing solution which was additionally purified by a hydrophobic interaction chromatography in negative chromatography mode, before the start of storage.

FIG. 1b: Fibrinogen-containing solution which was additionally purified by a hydrophobic interaction chromatography in negative chromatography mode, after storage at 30° C. for 2 months.

FIG. 1c: Initial fibrinogen-containing solution without additional purification by a hydrophobic interaction chromatography, after storage at 30° C. for 2 months.

The term fibrinogen preferably means human fibrinogen which can be purified for example from a mixture which contains fibrinogen and has been obtained from human blood. The term "mixture obtained from blood" means for example whole blood, blood plasma, plasma fractions or plasma precipitates. Fibrinogen from human plasma, cryoprecipitate or Cohn fraction 1 is particularly preferred. Fibrinogen can be isolated both from pooled plasma donations and from individual donations. Human fibrinogen can also be obtained from the milk of transgenic animals, see, for example, U.S. Pat. No. 5,639,940. Fibrinogen obtained by recombinant expression from cell culture, see, for example, U.S. Pat. No. 6,037,457, is also included. It is thus possible to isolate fibrinogen from the appropriate fermentation supernatants or fractions produced therefrom. However, fibrinogen isolated from a mixture which contains fibrinogen and has been obtained from animal blood, preferably from animals such as mammals (e.g. pig, horse, cattle, goat, sheep and dog), is also included.

Contaminating proteins mean for the purpose of the invention in principle all proteins which occur in plasma in addition to fibrinogen or appear in the milk of transgenic animals or in the cell culture supernatant. They are particularly preferably fibrinogen-degrading proteins able to degrade fibrinogen by proteolysis, or precursors of fibrinogen-degrading proteins (proenzymes) which must be previously activated for proteolytic degradation of fibrinogen, or activators of fibrinogen-degrading proteases. A proteolytic process results in fibrinogen degradation fragments which are smaller than fibrinogen and may have low molecular weights. It is possible in this connection for the alpha and/or beta and/or gamma chains of fibrinogen to be affected by the proteolytic degradation. Possible fibrinogen-degrading or degradation-assisting proteins or precursors thereof which may occur as possible contaminants in the purification of fibrinogen from plasma are, for example, plasmin, F XIa, callicrein, factor VII-activating protease (FSAP), F XIIa, plasminogen activators such as t-PA and u-PA, thrombin, metalloproteases (MMPs) and the corresponding precursors such as, for example, plasminogen, F XI, precallicrein, sc-FSAP, F XII, single-chain plasminogen activators such as sct-PA and scu-PA, prothrombin and pro-MMPs. In the following text, no distinction will be made between the activated forms and the respective precursors; on the contrary, the designation of the non-activated proenzymes will be used to represent both forms.

The process of the invention preferably makes possible through the process step(s) of the invention a depletion of fibrinogen-degrading proteases or the proenzymes and activators thereof. The latter may be for example plasminogen, F XI, precallicrein, F XII, pro-MMPs and/or plasminogen activators sct-PA and scu-PA. The depletion factor (DF) is above 1, preferably above 2. It is possible in this case for the proportion of F XII to be minimized, particularly preferably to □ 20 ng per $OD_{280-320}$. The proportion of F XI can be minimized to □ 1 ng per $OD_{280-320}$, particularly preferably to □ 0.2 ng per $OD_{280-320}$. The proportion of plasminogen can be reduced particularly preferably to levels of ☐ 5 ng per OD$_{280-320}$. The process step of the invention particularly preferably increases the stability of fibrinogen in solution and especially the proteolytic stability of the fibrinogen chains. The degradation fragments produced by the proteolysis of fibrinogen by fibrinogen-degrading proteins can be detected by various methods. Examples which may be mentioned here are fractionation in SDS polyacrylamide gels under reducing or non-reducing conditions, HPLC methods such as, for example, SEC (size exclusion chromatography) HPLC or immunological methods. The activity of remaining fibrinogen can moreover be determined by conventional methods as described by Clauss (Acta-Haematol. 17 (1957) 237-246). The depletion of fibrinogen-degrading proteins can be detected for example specifically with the aid of antibodies such as, for example, in the known ELISA (enzyme-linked immunosorbent assay) or RIA (radioimmunoassay) method. The antibodies are, for example, antibodies which are directed inter alia against the mentioned or further known fibrinogen-degrading proteases. The depletion can, however, also be detected nonspecifically by storing the fibrinogen solution in the liquid state and determining the degree of any degradation reaction after storage compared with a non-depleted control which has likewise been stored.

Chromatography means for the purposes of this invention a separation method in which a fibrinogen-containing solution is passed with the aid of a stream of liquid over a stationary phase, and constituents of the mixture become fractionated. The stationary phase is preferably the packing material in a chromatography column. The packing material, also called gel material hereinafter, consists of a solid support material composed of preferably approximately identically sized porous or nonporous particles on which functional groups which establish the mode of separation are present, covalently bonded. The support material may be for example biopolymers such as agarose, cellulose and dextran (preferably Sepharose and Sephadex), or synthetic polymers, such as, for example, methacrylate, polyvinylbenzene, polystyrene and polyacrylamide or inorganic polymers such as, for example, silica or porous glass beads. The solution in which the fibrinogen to be purified is dissolved with contaminating proteins, and possible washing buffers and equilibration buffers, are to be regarded as mobile phases. Negative chromatography means for the purposes of this invention that the stationary and the mobile phase are to be chosen so that, on the one hand, the interaction of fibrinogen with the stationary phase is as weak as possible or zero while, on the other hand, the interactions of one or more contaminating proteins with the stationary phase are stronger than that of fibrinogen. The fibrinogen thus mainly passes through the column and is located mainly in the flow-through (>50%), whereas one or more contaminating proteins are mainly bound to the stationary phase. The column is pretreated and equilibrated according to the requirements of the gel material before being loaded with the fibrinogen-containing solution. The equilibration buffer preferably corresponds to the solution in which the fibrinogen and the contaminating proteins are dissolved. In order to minimize fibrinogen losses, fibrinogen still remaining in the mobile phase of the column can be washed out, with the volume of the washing buffer preferably corresponding approximately to that of the column. The washing buffer preferably corresponds to the solution in which the fibrinogen and the contaminating proteins have been dissolved. The washing buffer can, where appropriate, be combined with the flow-through. The contaminating proteins bound to the stationary phase can be eluted with appropriate solutions, and the stationary phase can where appropriate be used several times for a negative chromatographic purification step, for cost-saving reasons, by regeneration. If regeneration is not possible or not economic, the used gel material is discarded. The proteins eluted from the stationary phase can, however, if required also be used as starting material for isolating these protein components. Protein concentrates can be obtained by further purification or process steps where appropriate. It is possible in this way to produce for example concentrates of plasminogen, F XII and F XI inter alia.

It is possible in principle to use for the stationary phase in the negative chromatography for the purposes of this invention any material which is able under the chosen conditions, in particular the choice of the mobile phase, to enter into stronger interactions with one or more contaminating proteins than with fibrinogen. The gel materials (stationary phases) included for the process step of the invention are those belonging to the groups of cation exchangers, hydrophobic gels or dye gels. There is a wide range of commercially available column materials or prepacked columns, e.g. from Amersham, Bio-Rad, Biosepra, Merck, Perseptive Biosystems, Pharmacia, Prometic, Toso Haas, which are to be regarded as included. Some have been tested by way of example in the presented examples. The mobile phases should be adapted to the respective gel materials. However, in general, pH values in the range between 5 and 9 are preferred. Correspondingly, the buffer systems to be chosen are those which buffer well in this range. Examples would be citrate, phosphate and tris buffers.

The negative chromatography process step is preferably carried out at a temperature between 2 and 30° C.

Cation exchangers are gel materials of ion exchange chromatography in which proteins compete with salt ions of the mobile phase for the charged positions on a stationary phase, the ion exchange matrix. Cation exchangers contain negatively charged groups and can therefore interact with positively charged groups of proteins. Interaction depends on the strength of the positive charge and the charge density on the surface of the cation exchanger and of the protein. Proteins carry positive or negative charges due to basic and acidic side groups of particular amino acids, with the total charge state depending on the pH of the solution. However, besides the amino acid composition, also post-translational modifications (such as, for example, phosphorylations) contribute to the isoelectric point (pI) of a protein, at which positive and negative charges neutralize each other. Fibrinogen has a pI of about 5.1-5.5 and belongs to the rather acidic proteins. Preferred cation exchangers comprise as exchange function (functional group, ligand) sulfomethyl groups (S types), sulfopropyl groups (SP types) or carboxymethyl groups (CM types). However, for the purposes of this invention, the range of cation exchangers also includes those with other suitable negatively charged functional groups such as, for example, heparin. Cation exchangers are described and commercially available from companies such as, for example, Amersham, Bio-Rad, Biosepra, Merck, Perseptive Biosystems, Pharmacia, Prometic or Toso Haas. Preferred cation exchangers are gels which can be sanitized in situ, such as, for example, Fractogel EMD SO$_3^-$650 (Merck), Macro-Prep 50 S (Bio-Rad), CM-Sepharose CL-6B (Pharmacia), Fractogel TSK CM 650 (Merck), Fractogel EMD CM, SP Sepharose, Heparin Fractogel (Merck) or Heparin-Sepharose CL 6B (Pharmacia).

The mobile phase with the cation exchanger should preferably be chosen so that fibrinogen has a negative total charge at the chosen pH and/or no or only slight interactions occur with the negatively charged groups of the stationary phase at the chosen ionic strength, whereas interactions still occur between the stationary phase and one or more contaminating proteins. The pH should be above pH 5.5 and particularly preferably above 6.0 and up to about 9. Salts which can be used are the salts known to the skilled worker for cation exchangers, particularly preferably NaCl. The salt concentration is preferably between 0 and 400 mM, particularly preferably between 0 and 100 mM.

Hydrophobic chromatography comprises the nonpolar surface regions of a protein interacting at usually relatively high salt concentrations with hydrophobic functional groups (ligands) of the stationary phase. The hydrophobic gel as stationary phase is preferably a synthetic polymer, silicate or a biopolymer such as, for example, Sepharose, whose surfaces are modified by hydrophobic ligands as functional group. The hydrophobic ligands are preferably alkyl groups having 1 to more than 24 carbon atoms (C), which may be linear or branched, or aromatic ligands. Possible examples are C1 (methyl), C3 (propyl), C4 (butyl), C5 (pentyl), C6 (hexyl) and C8 (octyl) groups, particularly preferably propyl, butyl, pentyl, hexyl and octyl groups. The alkyl groups may be derivatized, such as, for example, thiopropyl groups. Phenyl groups or aromatic compounds containing a phenyl derivative, such as, for example, phenylalanine groups, can preferably also be used. Phenyl groups may also be linked for example to alkyl chains. It is also possible to use for example pyridyl groups or derivatives thereof. Hydrophobic materials are extensively known to the skilled worker and commercially available for example from the companies Amersham, Bio-Rad, Biosepra, Merck, Perspective Biosystems, Pharmacia, Prometic and Toso Haas. Particularly preferred as stationary phase are, for example, Macro Prep Methyl HIC Support (Bio-Rad), Fractogel EMD Propyl 650 (Merck), Fractogel EMD Butyl 650 (Merck), Fractogel TSK Butyl 650 (Merck), Macro Prep t Butyl HIC Support (Bio-Rad), Butyl Cellufine (Amicon), Butyl Sepharose 4 Fast Flow (Pharmacia), Butyl S-Sepharose 6 Fast Flow (Prototyp, Pharmacia), HIC-Fractogel Pentyl (Merck), Hexyl S-Sepharose 6 Fast Flow (Prototyp, Pharmacia), Octyl Sepharose CL 4B (Pharmacia), Fractogel HW 65 Propyltentakel (Merck), Fractogel HW 65 Butyltentakel (Merck), Fractogel TA 650 (Merck), Phenyl Sepharose High Performance (Pharmacia), Phenyl Sepharose Fast Flow (Pharmacia), Phenylalanine Sepharose (Pharmacia), Thiopropyl Sepharose 6B (Pharmacia) or Pyridyl S-Sepharose 6 Fast Flow (Pharmacia).

The hydrophobic interaction of the proteins with the stationary phase is influenced not only by the functional groups (e.g. increasing chain lengths of alkyl groups enhances the hydrophobic nature), but also very greatly by ionic strength and pH of the solution forming the mobile phase. The mobile phase should be chosen, depending on the stationary phase used, so that one or more contaminating proteins enter into hydrophobic interactions with the stationary phase, whereas preferably more than 50% of fibrinogen passes through the column. Possible mobile phases and adaptations to the respectively stationary phase are known to the skilled worker. The pH should preferably be in the range above about 5 and up to about 9. Salts known for hydrophobic interaction chromatography can be used, particularly preferably for example NaCl, $Na_2SO_4$ and $(NH_4)_2SO_4$. The salt concentration is preferably in the range from 0.01 to 2 M, depending on the stationary phase.

Affinity chromatography involves specific, reversible adsorption of a protein (or of a protein group) onto an individual ligand which is bound to the support matrix. A suitable support matrix is, for example, Sepharose such as Sepharose 4B or Sepharose CL, whose OH groups can be used for covalent bonding of the ligand. Other suitable supports are known polymers such as, for example, Fractogel, Sephacryl, Cellufine or the like. Possible monospecific ligands are, for example, anti-bodies which are directed against fibrinogen-degrading proteins such as, for example, plasminogen, F XI, precallicrein or others. Affinity columns with antibodies are, however, costly on the industrial scale and can be employed economically efficiently only conditionally. Thus, within the framework of this invention, dyes which bind one or more contaminating proteins, in particular fibrinogen-degrading proteins, are included as group-specific ligands. Blue, red and green dye gels are particularly preferred. Examples of corresponding materials are Blue Sepharose 6FF (Pharmacia), Blue Sepharose CL 6B (Pharmacia), Blue Trisacryl Plus LA (Biosepra/Ciphergen), Blue Hyper D (Biosepra/Ciphergen), Mimetic Blue Agarose (Prometic), Mimetic Blue SA P6XL (Prometic), Mimetic Blue 1 P6XL (Prometic), Red Sepharose CL 6B (Pharmacia), Fractogel TSK AF Green (Merck) and/or Matrex gel Green A (Amicon). Further dye gels are sufficiently well known to the skilled worker and commercially obtainable or producible at the relevant manufacturers.

The pH of the mobile phase is preferably in the range from about 5 to about 9.

Negative adsorption for the purposes of this invention means that a fibrinogen-containing solution is mixed in a suitable container with an adsorbent material which adsorbs fibrinogen under the chosen conditions in only small amounts or not at all, whereas one or more contaminating proteins are adsorbed. Fibrinogen therefore remains predominantly in solution. This process is also known as discontinuous or batch process. The conditions for the adsorption should be chosen so that the contaminating proteins have sufficient time and opportunity to bind to the adsorbent material. For example, mixing can take place for example by cautious stirring at suitable temperatures. Suitable temperatures are for example between 2 and 30° C. It is possible to employ as adsorbent material in principle any material which is able under the chosen conditions to bind one or more contaminating proteins, and to bind fibrinogen in only small proportions or not at all. Materials include gel materials which have already been mentioned under chromatography and thus belong to the groups of cation exchangers, dye gels and hydrophobic gels. Preferred solutions correspond to preferred mobile phases for the chromatography. The adsorbent material with the bound, contaminating proteins can be separated from the fibrinogen-containing solution by methods known to the skilled worker. Mention may preferably be made here of the method of filtration, of centrifugation and/or sedimentation. The adsorbent material can preferably be regenerated by eluting the contaminants and changing the buffer, so that it can be used more than once. The proteins eluted from the adsorbent material can if required also be used as initial basis for isolating these protein components. It is thus possible by, where appropriate, further purification or process steps to obtain protein concentrates. It is possible in this way to produce for example concentrates of plasminogen, F XII, F XI, inter alia.

Negative adsorption in batch format is a technique which can be used in addition to or instead of negative chromatography.

The process steps of the invention usually make it possible for the step yield to be $\geq 50\%$ fibrinogen in the flow-through or in the supernatant, preferably $\geq 70\%$.

In a further embodiment, substances which weaken the binding of plasminogen to fibrinogen are added during the process of the invention and in particular during the process steps of the invention. It is known that fibrinogen tends to bind other proteins such as, for example, plasminogen. This repeatedly leads to partial copurification of contaminants such as plasminogen. Copurifications can be minimized by binding-weakening substances. These substances preferably include ω-amino acids such as ε-aminocaproic acid, in addition to tranexamic acid, PAMBA (p-aminomethylbenzoic acid), lysine and further lysine analogs.

It is known that enrichment and isolation of fibrinogen ordinarily requires a plurality of process steps, and there are numerous possible combinations of these individual purification steps. The process of the invention may comprise, besides one or more process step(s) of the invention, therefore additional process steps which are in principle to be found in the prior art for purifying fibrinogen and are included herewith. The state of the art on the purification of fibrinogen has already been substantially explained, and the correspondingly cited patents and publications are included herewith. Preferred process steps comprise no chromatography or adsorption in which fibrinogen binds to a large extent, and thus elution with all its disadvantages would be necessary.

In a preferred embodiment, the process of the invention comprises one or more process steps in which aluminum hydroxide $(Al(OH)_3)$ is added to the fibrinogen-containing solution to be purified. The $Al(OH)_3$ adsorbs primarily the factors of the prothrombin complex and can be removed for example by centrifugation and/or filtration.

In a preferred embodiment, the process comprises one or more process steps in which the fibrinogen is precipitated. It is particularly preferred to add glycine or other amino acids for the precipitation. If the glycine concentration is sufficiently high, this leads to direct precipitation of fibrinogen (one-stage glycine precipitation). However, an alternative or additional possibility is a two-stage glycine precipitation in which the glycine concentration in a first step is chosen so that fibrinogen substantially remains in the supernatant, and precipitated proteins are removed for example by centrifugation, and the major amount of the fibrinogen is precipitated only in a second step by increasing the glycine concentration, as also shown in the examples. As mentioned above it is also possible to use other amino acids instead of the amino acid glycine. Alanine, glutamine or glutamic acid may be mentioned here by way of example. However, other known precipitating agents (such as, for example, sodium chloride, ammonium sulfate or polyethylene glycol) can also be used in this case.

In a further preferred embodiment, the process comprises one or more process steps in which plasminogen is depleted via a gel material with lysine ligands or analogous ligands. Examples thereof would be lysine-Sepharose, Lys-Hyper D, Lys-Fractogel, aminohexyl-Sepharose or others. This leads to an advantageous depletion of plasminogen, which may additionally have advantageous effects on the stability of fibrinogen on storage in liquid form. In addition, depletion of plasminogen is also advantageous if the fibrinogen concentrate is to be employed as component of a fibrin glue.

In a further preferred embodiment, the process includes one or more process steps in which infectious particles which are potentially present, such as, for example, viruses, are inactivated or depleted as substantially as possible. If the fibrinogen is isolated from human plasma, this is a particularly preferred constituent of the process of the invention. Inactivation or depletion of infectious particles can take place by techniques known to the skilled worker, which are included herewith. These are processes such as, for example, pasteurization, heating in the dry state, nanofiltration, chemical additions (for example detergents), irradiations or combinations thereof.

In a further preferred embodiment, the process comprises one or more process steps which include an ultrafiltration and/or dialysis. These methods are advantageously employed in order to change the buffer of the fibrinogen-containing solution, i.e. change ingredients of the solution, or to concentrate the protein solution. This is particularly preferred for preparation for a purification step or at the end of the process of the invention, in order to choose formulation ingredients suitable for storage and use as pharmaceutical preparation.

Ultrafiltration also provides the opportunity in addition to deplete contaminating proteins by choosing filters which allow contaminating proteins to pass through, but retain fibrinogen, as described for example also in WO 93/17776. It was possible to show in the course of this invention that depletion of fibrinogen-degrading proteins is also possible if suitable filters are selected with a molecular weight limit (cutoff of, for example, 300 kDa. In a particularly preferred embodiment, therefore, filters with a molecular weight limit (cutoff) of from 50 to 500 kDa are employed for the ultrafiltration.

In a further preferred embodiment, the process comprises a sterilizing filtration. This is particularly worthwhile at the conclusion of the process to produce a pharmaceutical preparation.

In a preferred embodiment, a plurality of the process steps mentioned above are combined with one or more process steps of the invention to give a process of the invention. The sequence of individual process steps can moreover be varied. It is also possible for individual process steps, such as, for example, the precipitation, to be applied more than once. In a particularly preferred embodiment, a combination comprises, besides one or more process steps of the invention, at least the $Al(OH)_3$ adsorption steps, one- and/or two-stage glycine precipitations, and pasteurization. These process steps are advantageously combined with an affinity column with lysine ligands. After completion of the purification, the solution components are replaced by a solution suitable for storage. Possible methods such as, for example, dialysis, ultrafiltration, etc. are known to the skilled worker and included herewith. A sterilizing filtration can follow the purification. The purification process of the invention consists in a particularly preferred embodiment of the following process steps:

preparation of a plasma fraction
adsorption onto aluminum hydroxide
inactivation of infectious particles such as, for example, viruses
precipitation
further purification and/or inactivation steps
negative chromatography or chromatographies and/or negative adsorption(s)
ultrafiltration/diafiltration
sterilizing filtration In a particularly preferred embodiment, the further purification steps include an affinity column with lysine ligands such as, for example, Lys-Sepharose. Both the number and the sequence of individual process steps can be varied. Thus, for example, it would be possible for one or more negative adsorptions or chromatography steps to take place directly following the $Al(OH)_3$ adsorption. This would have the advantage that possible fibrinogen-degrading proteins are depleted at an early time and are thus no longer able to have an adverse effect on the stability of the fibrinogen in the subsequent course of the purification.

If the particularly preferred embodiments are used, the degradation of fibrinogen on storage of fibrinogen in liquid form at 30° C. for 1 month can be significantly reduced in the absence of added fibrinolysis inhibitors, i.e. significantly fewer low molecular weight degradation fragments are produced in this storage time. It can be shown by means of SEC-HPLC analysis that the increase in the proportion of low molecular weight degradation fragments compared with the remaining peaks is less than 2.5%, in particular less than 1.5%-2%, on use of the particularly preferred embodiments which additionally employ an affinity column with lysine ligands. This application therefore also relates to a fibrinogen concentrate or a corresponding pharmaceutical preparation with fibrinogen, which shows less than 2.5-3% fibrinogen degradation fragments, determined by means of SEC-HPLC, after storage in liquid form at 30° C. for 1 month, or increases by less than about 1.5-2.5% in degradation fragments based on the total peak area.

The invention further relates to fibrinogen which has been purified by the process of the invention. The fibrinogen obtained in this way, or a corresponding pharmaceutical preparation, preferably now comprises only ☐ 0.2 ng per $OD_{280-320}$ of F XI and/or $\leq$20 ng per $OD_{280-320}$ of F XII and/or $\leq$5 ng per $OD_{280-320}$ of plasminogen and/or $\leq$0.02 ng, preferably $\leq$0.01 ng, per $OD_{280-320}$ of t-PA.

The contaminating proteins which are bound to dye columns, cation exchangers or hydrophobic gels during the process step of the invention for purifying fibrinogen by means of negative chromatography or adsorption can be used as initial basis for isolating these protein components. Corresponding protein concentrates can be obtained by eluting the proteins from the corresponding gel material and, where appropriate, further purification or process steps. It is possible in this way to produce for example concentrates of plasminogen, t-PA, F XII or F XI. Accordingly, this application includes a process for isolating one or more plasma proteins, and production of corresponding pharmaceutical preparations using a gel material which binds one or more plasma proteins, does not bind fibrinogen under the chosen conditions, and is suitable for cation exchange chromatography, hydrophobic inter-action chromatography or affinity chromatography on dye columns.

The application further relates to the production of a pharmaceutical preparation which comprises fibrinogen which has been purified by the process of the invention. Possible pharmaceutical preparations are known to the skilled worker, and the additions depend on the planned use. The formulation ingredients known to the skilled worker and appropriate for an intravenous administration of fibrinogen may be different from those for use as fibrin glue. Account must also be taken of particular additions if intermediate storage is planned as lyophilizate, in the liquid or in the frozen state. Known lyophilization aids for proteins are, for example, saccharides such as sucrose, mannose, galactose and glucose, sugar alcohols such as, for example, mannitol or sorbitol or amino acids. Possible formulation ingredients for said storage forms are monovalent metal salts (for example sodium or potassium chloride), divalent metal salts (for example magnesium or calcium chloride), amino acids (for example glycine, arginine, aspartic acid, glutamic acid, histidine, lysine, isoleucine), carbohydrates (for example glucose, sucrose, trehalose, lactose, cellulose, sorbitol, mannitol and glycosaminoglycans), detergents (for example poloxamers or polysorbates), chaotropic agents (for example urea and guanidine or derivatives thereof), inhibitors such as, for example, aprotinin, alpha-2-antiplasmin, alpha-2-macroglobulin, alpha-1-antiplasmin, C1-inhibitor, antithrombin, plasminogen activator inhibitors (PAI), thrombin-activatable fibrinolysis inhibitor (TAFI) and lysine analogs such as ε-aminocaproic acid, plasma proteins (for example F XIII), antioxidants (for example ascorbic acid), buffer substances (for example amino acids such as arginine, buffer systems such as citrate, phosphate, acetate, succinate, tris(hydroxymethyl)aminomethane (tris), glycyl glycine, carbonate and bicarbonate) or mixtures thereof. The pH is preferably between about 5 and about 8.

The following additives are suitable for preparing the fibrinogen solution as ingredient of a liquid fibrin glue for example: NaCl (0-400 mM), $Na_3$-citrate (0-50 mM), L-Arg×HCl (0.1-1 M), $CaCl_2$ (0-10 mM), and, where appropriate, other stabilizing agents such as amino acids, carbohydrates and detergents.

The invention further relates to the use of fibrinogen or of a pharmaceutical preparation comprising fibrinogen which has been purified by a process comprising one or more of the process steps of the invention. Possible applications are known to the skilled worker, and the fibrinogen produced by the process of the invention can be employed for all known uses of fibrinogen. The medical use preferably relates to humans, but uses in veterinary medicine are also included. The fibrinogen preparation of the invention is generally suitable for the therapy of fibrinogen deficiency states. These deficiency states may arise for example in association with extensive wounds, with severe hemorrhages, with extensive burns, pathological activation of coagulation (consumption coagulopathy, also called DIC (disseminated intravascular coagulation)), through medicaments or severe liver disorders (e.g. with impaired synthesis due to liver parenchymal damage). Besides the described acquired hypofibrinogenemias (reduced fibrinogen in the blood) and afibrinogenemias (absence of or great diminution in fibrinogen in the blood) there are also rare cases of inborn afibrinogenemia or hypofibrinogenemia which may be caused by absence of or diminution in fibrinogen synthesis in the liver.

For hypofibrinogenemias and afibrinogenemias, the fibrinogen preparation of the invention is preferably injected intraveneously into the patient in order to compensate for corresponding fibrinogen deficiency states. Dosages are governed by the level of deficiency occurring.

Fibrinogen has great importance in the fibrin therapy as important component of so-called fibrin glues. The fibrin glue simulates the last step of the coagulation of blood since stabilized fibrin is formed on combination of fibrinogen with thrombin and aids such as calcium and F XIII.

There are diverse possible uses of fibrin glues in medicine which are sufficiently well known (see, for example, Sierra, Journal of Biomaterials Applications 7 (1993) 309-352; Martinowitz & Spotnitz, Thrombosis and Haemostasis 78 (1997) 661-666; Radosevich et al. Vox Sanguinis 72 (1997) 133-143). Those important to mention are hemostatis, wound closure, sealing of sutures and wound healing. Local intraoperative hemostatis is particularly important for parenchymatous organs and in the cardiovascular specialty. Even severe hemorrhages after injuries to the liver or spleen can be stopped in this way. Fibrin glues are also employed for the closure and fixation of skin wounds (including skin transplants) and for sealing sutures (e.g. on a duodenal stump). Mention may also be made by way of example of the use in the sealing of a plastic dural substitute and for sealing cavities and gluing the pleural membranes for palliative treatment of pleural effusions. The fibrin glues can also be employed advantageously for gluing connective tissues such as bones, cartilages and tendons. A fibrinogen component free of synthetic fibrinolysis inhibitors has its advantages for example in particular on application for dural sealing, because substances such as tranexamic acid have proved to be neurotoxic (Lit: M. G. Schlag, R. Hopf, U. Zifko and H. Redl; Acta Neurochir 144: 63-69 (2002)). Fibrin glues can, however, also be used to prevent postoperative adhesions.

Fibrinogen can also be used as a component for producing a fibrin matrix. Such a carrier material can be used for slow release of active substances such as, for example, growth factors (e.g. also together with osteoinductive proteins as matrix for bone and/or cartilage regeneration), antibiotics, cytostatics, antiinflammatory additions and/or additions which promote wound healing. The carrier can also consist of a mixture of fibrin with other materials.

A fibrin matrix additionally has extensive possible uses in biotechnology, such as, for example, as support material and culture medium for cells and tissues in tissue engineering or for enveloping implants such as, for example, biosensors.

The fibrinogen of the invention can also be used as component of a diagnostic aid.

The invention is additionally to be illustrated by the following examples which are, however, not intended to have any restrictive effect.

EXAMPLE 1

This example shows that cation exchanger materials and hydrophobic gels and dye gels are able to purify a fibrinogen-containing solution by means of negative chromatography in such a way that the stability of the fibrinogen is increased compared with the starting material.

Fibrinogen starting material was obtained by preparation of a pasteurized fibrinogen concentrate and fractional precipitation by addition of glycine as described in EP 0 103 196.

The fibrinogen-rich precipitate was firstly dissolved in a suitable aqueous solvent (50 mM NaCl; 20 mM trisodium citrate dihydrate, 0.05% $NaN_3$ pH 7.3) and served as starting material for the further purification steps using negative chromatography.

The chromatography columns (Ø0.7 cm) used for this purification were each packed with 1.0 ml of the respective gel material. The columns were equilibrated in one of buffers 1-3, depending on the respective gel material.

| Buffer 1: | 50 mM NaCl, 50 mM sodium phosphate pH 7.4 for cation exchanger and comparison column |
| --- | --- |
| Buffer 2: | 1000 mM NaCl, 50 mM sodium phosphate pH 6.5 for hydrophobic gels |
| Buffer 3: | 50 mM sodium phosphate pH 7.4 for dye gels |

30-40 ml portions of fibrinogen-containing solution were dialyzed against the appropriate buffers (1-3) (see table 1) and diluted with the appropriate buffers to an $OD_{280-320}$ of 10. 15 ml of this fibrinogen solution were loaded onto each column, and the columns were each washed with 1.0 ml of the respective buffer (1-3). The column flow-through and the washing solution were combined. Firstly, the optical density was measured in a photometer at 280 and 320 nm ($OD_{280-320}$) in order to determine the yield (in %) compared with the starting material. An aliquot of this material was retained to determine the 0 value for the analysis of the subsequent storage test. The column flow-through combined with the respective washing solutions, and the starting material were dialyzed against a buffer comprising 100 mM NaCl, 20 mM $Na_3$ citrate, 5% L-Arg pH 7.2, and 1 ml portions thereof were mixed with sodium azide (final concentration 0.05% w/v). These differently purified fibrinogen preparations, and the starting material as control, were stored at +30° C. for storage times of up to 3 months. The stability of fibrinogen was determined in each case by means of SEC-HPLC after the appropriate storage periods. This involves a size exclusion chromatography (SEC) which fractionates the proteins and cleavage products which are present according to their molecular weight. Low molecular weight fragments resulting from proteolytic degradation of fibrinogen appear as a new peak (fragment peak 4) and, where appropriate, further new peaks with increased retention time. The area of the fragment peaks (≦peak 4) was determined and calculated as a percentage of all the peaks. The value was corrected for the small proportion before storage started (zero value), and the values found in this way are shown as result in table 1. They reflect the increase in degradation fragments during storage under accelerated conditions.

The analysis was carried out using an appropriate HPLC system with a SEC column (TSK gel G 4000 SWXL, 7.5×300 mm from TOSO HAAS). The proteins and protein fragments were fractionated after appropriate storage times at a flow rate of 0.5 ml/min in a suitable running buffer at 20-25° C. The protein and protein fragment peaks were detected at 280 nm.

FIG. 1 shows by way of example typical fibrinogen separation runs using SEC HPLC. It shows a fractionation of a fibrinogen-containing solution which was purified with the aid of lysine-Sepharose chromatography and a negative HIC before storage started (t=0, zero value, FIG. 1a) and after storage at 30° C. for 2 months (t=2 months, FIG. 1b).

FIG. 1c by contrast shows the fractionation of a fibrinogen-containing solution without additional purification via negative HIC after storage at 30° C. for 2 months (t=2 months). The zero value (t=0) for this fibrinogen-containing solution is not shown because it shows a separation result comparable with FIG. 1a.

The main peak at a retention time of about 15-16 min corresponds to fibrinogen. The peak with a retention time of about 24 min, and peaks with higher retention times, are fibrinogen degradation fragments. It is clear from FIG. 1b that the area under the peaks corresponding to the degradation fragments after storage at 30° C. for 2 months is distinctly reduced through use of the hydrophobic gel compared with the control material without HIC purification, which was likewise stored at 30° C. for 2 months (FIG. 1c). The smaller occurrence of degradation fragments is to be regarded as proof of the greater stability of fibrinogen after purification by negative HIC.

TABLE 1

| Gel material | Buffer | Yield (%) | Increase in degradation fragments (% of all peaks) δ (≦peak 4) after 2 mon | δ (≦peak 4) after 3 mon |
| --- | --- | --- | --- | --- |
| Cation exchanger | | | | |
| Fractogel EMD $SO_3$ 650 | 1 | 78 | 4.1 | 6.0 |
| Heparin Fractogel | 1 | 91 | 4.2 | 6.4 |
| Hydrophobic gel | | | | |
| Fractogel TA 650 | 2 | 81 | 4.3 | 5.8 |
| Butyl Cellufine | 2 | 73 | 3.9 | 6.4 |
| Fractogel EMD Butyl 650 | 2 | 82 | 4.1 | 5.9 |
| Fractogel EMD Propyl 650 | 2 | 91 | 3.8 | 5.7 |
| Macro Prep Methyl | 2 | 92 | 3.9 | 6.5 |
| Macro Prep t Butyl | 2 | 94 | 3.3 | 5.6 |
| Butyl Sepharose 4 Fast Flow | 2 | 82 | 4.1 | 6.2 |
| Thiopropyl Sepharose 6B | 2 | 96 | 4.3 | 6.4 |
| Butyl-S-Sepharose 6 Fast Flow (Prototype) | 2 | 88 | 3.8 | 5.9 |
| Octyl Sepharose CL 4B | 2 | 91 | 4.0 | 6.1 |
| Phenyl Sepharose High Performance | 2 | 77 | 4.3 | 6.3 |
| Phenylalanine Sepharose | 2 | 91 | 4.0 | 6.7 |

TABLE 1-continued

| Gel material | Buffer | Yield (%) | Increase in degradation fragments (% of all peaks) δ (≦peak 4) after 2 mon | δ (≦peak 4) after 3 mon |
|---|---|---|---|---|
| Hexyl S-Sepharose 6 Fast Flow | 2 | 57 | 3.6 | 5.8 |
| Pyridyl S-Sepharose Fast Flow | 2 | 68 | 3.5 | 5.5 |
| Dye gels | | | | |
| Blue Hyper D | 3 | 68 | 4.8 | 5.7 |
| Fractogel TSK AF Green | 3 | 60 | 6.1 | 9.3 |
| Blue Sepharose CL 6B | 3 | 85 | 3.0 | 5.1 |
| Red Sepharose CL 6B | 3 | 73 | 3.9 | 6.4 |
| Starting material | SM | | 16.8 | >90 |
| Lysine-Sepharose 4B (comparison column) | 1 | 98 | 6.7 | 11.2 |

Table 1 shows that the increase in the proportion of degradation fragments with increased retention time is distinctly less after purification of the fibrinogen used on one of the gel materials mentioned than for the control (starting material). The increased stability of fibrinogen demonstrated thereby compared with the control (starting material before negative chromatography) is clearly to be found after only 1 month, but then increases further with longer storage times. It is also possible in some cases to discriminate between the various qualities of column materials after longer storage times of 3 months, but with a tendency after only 2 months. Improvements can be achieved even compared with the affinity chromatography, known in the state of the art, using lysine-Sepharose 4B which depletes plasminogen. Very good yield results, usually above about 70%, are also achieved throughout. The example additionally makes it clear that it is possible with a large number of different cation exchangers, hydrophobic gels and dye gels to achieve a substantial stabilization of fibrinogen and thus reduction in the formation of degradation fragments, so that it can be assumed that improved stability results can be achieved generally with support materials from the group of chromatographic separation principles mentioned.

EXAMPLE 2

In this example, further blue dye gels were tested and, in addition, the buffer conditions of the mobile phases for the cation exchanger Fractogel EMD $SO_3^-$650 (M) and the hydrophobic gel phenyl Sepharose HP used in example 1 were varied. The improved stability of fibrinogen was again established through the reduced formation of degradation fragments during a storage test. An additional check was made of whether fibrinogen-degrading proteins or the inactive precursors thereof (proenzymes) are depleted.

The starting material used was fibrinogen which, in addition to the analogous purification from example 1, was also purified on lysine-Sepharose after being taken up in a suitable aqueous solvent (50 mM NaCl; 20 mM trisodium citrate, 0.05% $NaN_3$ pH 7.4, buffer SM in table 2) and preferably after dialysis against the solvent.

The chromatography columns used (column body Ø=0.7 cm, h=2.5 cm from Qiagen) were each packed with 1.0 ml of the respective gel material. The gel material was equilibrated with the appropriate buffers.

Equilibration Buffers:

| | | | |
|---|---|---|---|
| 1a: | 50 mM NaCl, | 20 mM $Na_3$ citrate, | 0.05% $NaN_3$ pH 7.5 |
| 1b: | 50 mM NaCl, | 20 mM $Na_3$ citrate, | 0.05% $NaN_3$ pH 6.5 |
| 2a: | 50 mM NaCl, | 20 mM $Na_3$ citrate, | 0.05% $NaN_3$ pH 6.5 |
| 2b: | 50 mM NaCl, | 20 mM $Na_3$ citrate, | 0.05% $NaN_3$ pH 7.0 |
| 2c: | 50 mM NaCl, | 20 mM $Na_3$ citrate, | 0.05% $NaN_3$ pH 7.5 |
| 2f: | 150 mM NaCl, | 20 mM $Na_3$ citrate, | 0.05% $NaN_3$ pH 7.5 |
| 3a: | 50 mM NaCl, | 20 mM $Na_3$ citrate, | 0.05% $NaN_3$ pH 6.5 |
| 3b: | 50 mM NaCl, | 20 mM $Na_3$ citrate, | 0.05% $NaN_3$ pH 7.5 |
| 3c: | 500 mM NaCl, | 20 mM $Na_3$ citrate, | 0.05% $NaN_3$ pH 7.5 |
| 3d: | 1000 mM NaCl, | 20 mM $Na_3$ citrate, | 0.05% $NaN_3$ pH 7.5 |

The fibrinogen-containing loading solution was, where appropriate, approximated to the above buffer conditions by adding NaCl and adjusting the pH, and a volume of solution corresponding to an amount of protein of 150 or 300 $OD_{280-320}$ per ml of gel (see table 2) with an unrestricted drop rate. The columns were washed with in each case 1 ml of the appropriate buffer. The washing solution was combined with the respective flow-through and dialyzed against 50 mM NaCl, 20 mM $Na_3$ citrate, 0.05% $NaN_3$ pH 7.4 at 4° C. overnight. Storage took place at 30° C. for storage times of various lengths (0-2 months (mon)).

Analysis with the aid of SEC-HPLC took place as described in example 1.

In addition, the amount of plasminogen, factor XI and factor XII was determined by ELISA measurements. In a sandwich ELISA, plasminogen was initially bound to rabbit polyclonal antibodies (IgG preparation from Dade Behring) which were immobilized as capture antibodies on a microtiter plate. Detection took place with the aid of the same polyclonal antibody preparation but labeled with peroxidase. F XII was determined using the F XII ELISA kit from Kordia Life Sciences (Netherlands) in accordance with the manufacturer's information. Likewise, F XI was quantified using the F XI ELISA kit from Kordia Life Sciences (Netherlands) in accordance with the manufacturer's information.

The depletion factor (DF) is the ratio of the amount of protein (e.g. plasminogen, F XI or F XII) determined per $OD_{280-320}$ in the starting material and the amount of protein determined per $OD_{280-320}$ in the fibrinogen-containing solution after the respective negative chromatography.

The results are shown in table 2.

TABLE 2

| Gel material | Buffer | Loading of the column $OD_{280-320}$ | Yield (%) | δ peak 4 after 1 mon/ 30° C. | δ peak 4 after 2 mon/ 30° C. | Plasminogen DF | F XII DF | F XI DF |
|---|---|---|---|---|---|---|---|---|
| Blue Hyper D | 1a | 150 | 61 | 1.03 | 2.25 | 3.7 | 21.5 | 2.0 |
| Mimetic Blue | 1a | 150 | 94 | 1.18 | 2.68 | 1.6 | 1.3 | ≧2.2 |

TABLE 2-continued

| Gel material | Buffer | Loading of the column OD$_{280-320}$ | Yield (%) | δ peak 4 after 1 mon/ 30° C. | δ peak 4 after 2 mon/ 30° C. | Plasmino-gen DF | F XII DF | F XI DF |
|---|---|---|---|---|---|---|---|---|
| SA P6XL Blue Trisacryl Plus LS | 1a | 150 | 74 | 1.13 | 2.42 | 2.4 | 22.1 | ≧2.2 |
| Blue Sepharose 6FF | 1a | 150 | 74 | 1.13 | 2.47 | 4.0 | 9.5 | ≧2.2 |
|  | 1b | 150 | 61 | 1.12 | 2.75 | 2.4 | 12.6 | ≧2.2 |
| Fractogel EMD SO$_3$.650 | 2a | 150 | 45 | 1.57 | 2.63 | 3.8 | 12.4 | ≧2.2 |
|  | 2b | 150 | 56 | 1.51 | 2.64 | 3.2 | 15.1 | ≧2.2 |
|  | 2c | 150 | 80 | 1.06 | 2.68 | 1.8 | 1.6 | ≧2.2 |
|  | 2f | 150 | 94 | 1.58 | 3.52 | 2.1 | 1.2 | ≧2.2 |
| Phenyl Sepharose High Performance | 3a | 150 | 87 | 1.32 | 3.03 | 2.4 | 1.8 | 1.3 |
|  | 3b | 150 | 91 | 1.30 | 3.10 | 2.0 | 1.1 | 1.3 |
|  | 3c | 150 | 76 | 1.17 | 2.81 | 1.7 | 0.9 | 1.7 |
|  | 3d | 150 | 66 | 1.09 | 2.69 | 1.8 | 0.9 | ≧2.2 |
|  | 3b | 300 | 96 | 1.43 | 3.27 | 2.0 | 1.2 | 1.5 |
| Starting material | SM | — | — | 1.85 | 4.33 | — | — | — |

DF: depletion factor

As is evident from table 2, the use of the other tested blue dye gels is also suitable for diminishing the occurrence of degradation fragments, i.e. for achieving an increased stability of fibrinogen. At the same time it is demonstrated by way of example that plasminogen, F XII and F XI can be depleted—also to different extents—through the negative chromatographies used, with appropriate choice of the separation parameters.

As expected, the efficiency of the cation exchanger (Fractogel EMD SO$_3$⁻650) shows a dependence on the mobile phase (buffer composition). Good depletion of plasminogen and F XII can be demonstrated when the pH of the mobile phase is about 6.5-7.5. If the pH of the separation is raised, the stability of the fibrinogen on storage in the liquid state decreases but is still distinctly better than for the starting material. Since, on the other hand, the yield of fibrinogen decreases at low pH values because the interactions of fibrinogen with the functional groups increase and it is partly adsorbed onto the column material, the best conditions in the case of the cation exchanger Fractogel EMD SO$_3$⁻650 (M) for the mobile phase are in the pH range around 7.0. Although a simultaneous increase in the salt concentration improves the yield of fibrinogen, at the same time the stability decreases somewhat. Thus, in the case of Fractogel EMD SO$_3$⁻650 (M), the salt concentration would preferably remain in the region of about 50 mM NaCl, and for example the amount loaded per ml of gel would be increased to improve the yield. It is similarly possible to test optimal compositions of the mobile phases for other cation exchangers too.

Hydrophobic gels also show a dependence on the mobile phase, especially on the salt concentration of the buffer. With phenyl Sepharose HP for example it is possible to achieve a depletion of plasminogen and an increased stability of fibrinogen, with a good yield of fibrinogen, over a wide range of NaCl. All the chosen conditions lead to an increased stability compared with the starting material, so that in principle a plurality of conditions can be employed advantageously. Other hydrophobic gels and/or other buffer conditions can be optimized in a similar way.

It is further evident from the table that the different gels in this example contribute to a different extent of plasminogen, F XII and F XI depletion. Particularly efficient depletion of F XII was achievable for example through the blue dye gels Blue Hyper D and Blue Trisacryl Plus LS, Blue Sepharose 6FF or cation exchangers such as Fractogel EMD SO$_3$⁻650 (M).

EXAMPLE 3

In this example, further dye, cation exchanger and hydrophobic gels, and conditions for the negative chromatography, were tested.

The starting material was obtained by the same purification scheme as described in example 2. The columns were equilibrated, as already described in example 2, with the respective buffer detailed below.

| | | | |
|---|---|---|---|
| 1: | 50 mM NaCl, | 20 mM Na$_3$ citrate, | 0.05% NaN$_3$ pH 7.5 |
| 2: | 50 mM NaCl, | 20 mM Na$_3$ citrate, | 0.05% NaN$_3$ pH 7.0 |
| 3a: | 1000 mM NaCl, | 20 mM Na$_3$ citrate, | 0.05% NaN$_3$ pH 7.5 |
| 3b: | 2000 mM NaCl, | 20 mM Na$_3$ citrate, | 0.05% NaN$_3$ pH 7.5 |

The starting material was dialyzed against the appropriate buffers. The chromatography columns were in each case loaded with an OD$_{280-320}$ of 150 or 300 (equivalent to 15 ml or 30 ml) per ml of gel at an unrestricted drip rate. The first 0.5 ml of the column flow-throughs were discarded. The columns were washed with 1 ml of the respective buffer. The washing solution was combined with the respective flow-through and dialyzed against 50 mM NaCl, 20 mM Na$_3$ citrate, 0.05% NaN$_3$ pH 7.4 at 4° C. overnight. Storage took place at 30° C. for a storage time of 2 months.

Analysis with the aid of SEC-HPLC took place as described in example 1, and determination of the depletion factors (DF) for plasminogen, F XII and F XI took place as described in example 2.

TABLE 3

| Gel material | Buffer | Loading of the column $OC_{280-320}$ | Gel volume (ml) | Yield (%) | Plasminogen DF | F XII DF | F XI DF | δ peak 4 after 2 mon/ 30° C. |
|---|---|---|---|---|---|---|---|---|
| Blue Uniflow | 1 | 150 | 1.0 | 85 | 1.5 | 15.4 | 2.7 | 1.63 |
| Blue Trisacryl Plus LS | 1 | 150 | 1.0 | 77 | 4.8 | >45.3 | >4.3 | 1.55 |
| Fractogel EMD $SO_3$-650 (M) | 2 | 150 | 1.0 | 72 | 1.1 | 29.2 | >4.3 | 1.64 |
|  | 2 | 300 | 1.0 | 82 | 1.5 | 7.7 | >4.3 | 2.02 |
| Macro Prep t Butyl HIC Support | 3a | 150 | 1.0 | 100 | 0.8 | 1.1 | 1.4 | 2.11 |
|  | 3b | 150 | 1.0 | 89 | 1.1 | 1.3 | 1.6 | 2.08 |
| Fractogel EMD Butyl 650 (S) | 3a | 150 | 1.0 | 91 | 1.4 | 1.5 | 1.8 | 1.63 |
| Starting material | SM | — | — | — | — | — | — | 2.32 |

Table 3 shows that the other tested gels and conditions are also suitable for diminishing the appearance of degradation fragments. An increase in the amount loaded (loading of the column) leads to an improved yield.

EXAMPLE 4

Some gel materials which proved suitable in examples 1 to 3 were tested for their usability on a larger scale. Chromatography columns with a gel volume of about 500 ml were used for this, and the fibrinogen-containing solution was pumped through the columns.

A fibrinogen-containing solution was obtained by working up cryoprecipitate in accordance with EP 0 103 196 as far as the pasteurized fibrinogen solution.

The fibrinogen solution which had been pasteurized was mixed with three times the volume of diluting solution (3.5 g/l NaCl; 5.88 g/l trisodium citrate dihydrate in water, pH 7.5). 90 g of glycine per liter of diluted solution were added while stirring. The resulting precipitate was removed by centrifugation or filtration and discarded.

The supernatant was brought optionally to 200 mM L-Lys× HCl or EACA by adding solid L-Lys×HCl or EACA. A further 75 g of glycine were added per liter. The fibrinogen-rich precipitate was obtained by centrifugation and stored at −25° C. until processed further.

For further purification and depletion of traces of plasminogen, the fibrinogen-rich precipitate was dissolved and, preferably after dialysis against buffer solution (20 mM trisodium citrate, 50 mM NaCl pH 7.4, optionally containing 0.05% $NaN_3$ as preservative), pumped over a chromatography column with a matrix having L-lysyl radicals as ligands. The flow-through was used further for the subsequent steps.

To remove further contaminants which influence the stability of fibrinogen, the fibrinogen-containing solution was pumped over various second chromatography columns, where appropriate previously changing the buffer composition:

A: The fibrinogen-containing solution was pumped directly over a column (Ø 6 cm, volume about 735 ml) with blue dye gel which has a matrix carrying a derivatized anthraquinone dye as ligand (such as, for example, blue agarose from Prometic), and the flow-through was collected. The column was washed with 1 column volume (CV) of buffer solution (20 mM trisodium citrate, 50 mM NaCl pH 7.4, optionally containing 0.05% $NaN_3$ as preservative).

B: The fibrinogen-containing solution was adjusted to a pH of 6.7 by adding 0.1 M HCl and pumped over a column (Ø6 cm, volume about 500 ml or Ø6 cm, volume about 147 ml) with a matrix having $SO_3^-$ groups as ligands (Fractogel EMD $SO_3^-$650 (M)). The flow-through was collected. The column was washed with 1 CV of buffer solution (20 mM trisodium citrate, 50 mM NaCl pH 6.5, optionally containing 0.05% $NaN_3$ as preservative).

C: The fibrinogen-containing solution was adjusted to a final concentration of 1 M NaCl by adding crystalline NaCl and pumped over a column (Ø6 cm, volume about 500 ml) with a hydrophobic matrix which has phenyl groups as ligands (phenyl-Sepharose HP) and the flow-through was collected. The column was washed with 1 CV of buffer solution (20 mM trisodium citrate, 1 M NaCl pH 7.4, optionally containing 0.05% $NaN_3$ as preservative).

D: The fibrinogen-containing solution was adjusted to a final concentration of 1 M NaCl by adding crystalline NaCl and pumped over a column (Ø7 cm, volume about 577 ml) with a hydrophobic matrix which has butyl groups as ligands (Macro Prep t Butyl HIC resin) and the flow-through was collected. The column was washed with 1 CV of buffer solution (20 mM trisodium citrate dihydrate, 1 M NaCl pH 7.4, optionally containing 0.05% $NaN_3$ as preservative).

Fibrinogen preparations were produced by combining the fibrinogen-containing flow-throughs with the respective washing solutions and initially bringing to a protein concentration of about $OD_{280-320\ nm}$=2-200, preferably about 20-160, by suitable ultrafiltration processes, depending on the use, and subsequently dialyzed against solutions which contained the following formulation ingredients: NaCl, $Na_3$ citrate×$2H_2O$, L-Arg×HCl, optionally $CaCl_2$.

Final concentration and sterilizing filtration resulted in fibrinogen preparations which were tested by SEC-HPLC (see example 1) for the content of fibrinogen degradation fragments after storage at 30° C. for 1 month (see table 4).

TABLE 4

| Gel material | Buffer | δ (≤peak 4) after 1 mon/30° C. |
|---|---|---|
| Blue Agarose | 20 mM $Na_3$ citrate, 100 mM NaCl, 50 g/l L-Arg×HCl, 2.5 mM $CaCl_2$ pH 7.2 | 0.9 |

TABLE 4-continued

| Gel material | Buffer | δ (≦peak 4) after 1 mon/30° C. |
|---|---|---|
| Fractogel EMD SO$_3$ 650 (M) | 20 mM Na$_3$ citrate, 100 mM NaCl, 50 g/l L-ArgxHCl, 2.5 mM CaCl$_2$ pH 7.2 | 1.0 |
| Phenyl Sepharose High Performance | 20 mM Na$_3$ citrate, 100 mM NaCl, 50 g/l L-ArgxHCl, 2.5 mM CaCl$_2$ pH 7.2 | 1.2 |
| Macroprep-t Butyl HIC Support | 20 mM Na$_3$ citrate, 100 mM NaCl, 50 g/l L-ArgxHCl, 2.5 mM CaCl$_2$ pH 7.2 | 1.1 |
| Without additional negative chromatography | 20 mM Na$_3$ citrate, 100 mM NaCl, 50 g/l L-ArgxHCl, 2.5 mM CaCl$_2$ pH 7.2 | 2.6 |

The results show that it is possible even on the larger scale through use of negative chromatographies to reduce the difference of the degradation fragments (δ(≦peak 4)) produced after accelerated storage for 1 month to below 2%, and thus the stability of fibrinogen in solution on storage at 30° C. is distinctly increased.

EXAMPLE 5

In this example, two negative adsorptions in batch format using a dye gel and a hydrophobic gel were combined.

A fibrinogen-containing solution was obtained by adsorbing cryoprecipitate as starting material twice with Al(OH)$_3$, as described in EP 0 103 196.

Contaminating proteins such as, in particular, fibrinogen-degrading proteins were reduced/removed by carrying out further adsorptions in batch format. The gel material used for this was Blue Sepharose 6 FF which has a derivatized anthraquinone dye as ligand. 0.5 g of filter-moist gel was added per 10 g of fibrinogen-containing solution. (Subsequent stirring time: 90 min). The dye gel was then removed by centrifugation (20 min at 25° C. and 1500 g).

The fibrinogen-containing supernatant was subjected to a further negative adsorption. Phenyl Sepharose HP was used for this. The gel material was likewise employed in the ratio of 0.5 g per 10 g of fibrinogen-containing solution. (Subsequent stirring time: 90 min). Following the adsorption, the gel material with the bound contaminating proteins was removed by centrifugation.

The subsequent pasteurization and glycine precipitation were carried out in accordance with EP 0 103 196, with the exception that the precipitation took place in the presence of 200 mM Lys.

For further purification and plasminogen removal, the fibrinogen-rich precipitate was initially dissolved in a suitable aqueous solvent, filtered and, preferably after dialysis against buffer solution (20 mM trisodium citrate dihydrate, 50 mM NaCl, pH 7.4, optionally containing 0.05% NaN$_3$ as preservative) and adjustment of an optical density of about 10, pumped over a chromatography column with a gel material which has L-lysyl radicals as ligands.

Fibrinogen preparations were produced by initially bringing the fibrinogen-containing solution to a protein concentration of about OD$_{280-320\ nm}$=2-200, preferably about 20-160, by suitable ultrafiltration processes, depending on the use, and subsequently dialyzing against solutions which contained the formulation ingredients mentioned in example 4.

Sterilizing filtration resulted in fibrinogen preparations which were tested for stability with the aid of SEC-HPLC in accordance with example 1. This revealed a proportion of degradation fragments of <1.0%, measured on the basis of peak 4 and smaller peaks, which is distinctly less than with corresponding control workups, after storage at 30° C. for 1 month and after subtraction of the zero values.

It was possible to show with this example that negative adsorptions in batch format can also be used in order to achieve maximum stability of fibrinogen in solution. It was additionally shown that a plurality of negative adsorptions can be combined. It is further evident that process steps with negative adsorptions and/or negative chromatographies can reasonably integrate at various points in the process for purifying fibrinogen. Thus, in this example, in contrast to previous examples, negative adsorption is used very early in the purification process, immediately after the aluminum hydroxide treatment. Pasteurization, precipitation with glycine and removal of further plasminogen by lysine-Sepharose took place only thereafter.

EXAMPLE 6

This example investigated the extent to which fibrinogen-degrading proteins can be depleted with the aid of ultrafiltration through selection of suitable pore sizes.

A fibrinogen-containing solution was obtained by proceeding in accordance with example 1 up to and including the preparation of a pasteurized precipitate.

For further purification and depletion of fibrinogen-degrading proteins, the fibrinogen-rich precipitate was initially dissolved in a suitable aqueous solvent and subjected to intensive diafiltration, using ultrafiltration membranes with a cut-off of 300 kDa, against buffer solution (20 mM trisodium citrate dihydrate, 50 mM NaCl pH 7.4, optionally containing 0.05% NaN$_3$ as preservative).

Plasminogen was removed by pumping the solution over a chromatography column with a gel material which has L-lysyl radicals as ligands.

Fibrinogen preparations were produced by initially bringing the fibrinogen-containing solution to a protein concentration of about OD$_{280-320\ nm}$=2-200, preferably about 20-160, by means of suitable ultrafiltration processes and membranes (cutoff=300 kDa), depending on the use, and subsequently dialyzing against solutions which contained suitable formulation ingredients.

Final concentration and sterilizing filtration resulted in fibrinogen preparations which were tested for the content of fibrinogen degradation fragments with the aid of SEC-HPLC (see example 1) before the start of storage and after storage at 30° C. for 1 month. This revealed, after subtraction of the zero value, a reduced proportion of degradation fragments compared with a control with conventional ultrafiltration.

It was thus possible to show that further fibrinogen-degrading proteins can be depleted, and a more stable fibrinogen concentrate can be produced, by ultra-filtration with a cutoff of 300 kDa.

EXAMPLE 7

A fibrinogen precipitate was prepared as described in example 1 and was additionally purified by negative chromatography on Lys-Sepharose. After making up to 1 mol of sodium chloride per liter of fibrinogen solution, the latter was put onto a chromatography column packed with butyl-Sepharose and washed with buffer. The flow-through of the column was concentrated, dialyzed and tested for the content of t-PA, plasminogen and F XI. A comparative workup was carried out as control, in which the negative chromatography on butyl-Sepharose was not carried out. It was possible to show as result that the additional HIC distinctly reduced the concentration of t-PA, plasminogen and F XI, and that the stability is increased after storage at 30° C. (the proportion of fibrinogen fragments after 1 month at 30° C. was about 20% less when the HIC was carried out).

| | t-PA (ng/OD280-320) | Plasminogen (ng/OD280-320) | F XI (ng/OD280-320) | Fibrinogen fragments after 1 month at 30° C. (workup without HIC = 100%) |
|---|---|---|---|---|
| Workup without HIC | 0.046 | 2.47 | 0.069 | 100% |
| Workup incl. HIC | 0.003 | 2.04 | 0.038 | 79% |

EXAMPLE 8

A fibrinogen precipitate is prepared and purified by negative chromatography on Lys-Sepharose as described in example 1. Further purification takes place by means of a dye column, HIC and/or cation exchanger. The fibrinogen solution is transferred by diafiltration and ultrafiltration into the following formulation buffers and, after sterilizing filtration, subjected to accelerated storage at 30° C.:

1. 20 mM $Na_3$ citrate, 100 mM NaCl, 50 g/l L-Arg×HCl pH 7.2
2. 20 mM $Na_3$ citrate, 100 mM NaCl, 70 g/l L-Arg×HCl pH 7.2
3. 20 mM $Na_3$ citrate, 100 mM NaCl, 100 g/l L-Arg×HCl pH 7.2
4. 20 mM $Na_3$ citrate, 100 mM NaCl, 50 g/l L-Arg×HCl, 2.5 mM $CaCl_2$ pH 7.2
5. 20 mM $Na_3$ citrate, 100 mM NaCl, 70 g/L-Arg×HCl, 2.5 mM $CaCl_2$ pH 7.2
6. 20 mM $Na_3$ citrate, 100 mM NaCl, 100 g/l L-Arg×HCl, 2.5 mM $CaCl_2$ pH 7.2
7. 4 mM $Na_3$ citrate, 100 mM NaCl, 50 g/l L-Arg×HCl, 0.5 mM $CaCl_2$ pH 7.2
8. 12 mM $Na_3$ citrate, 100 mM NaCl, 50 g/l L-Arg×HCl, 1.5 mM $CaCl_2$ pH 7.2
9. 20 mM $Na_3$ citrate, 100 mM NaCl, 50 g/l L-Arg×HCl, 2.5 mM $CaCl_2$ pH 7.2
10. 20 mM $Na_3$ citrate, 200 mM NaCl, 50 g/l L-Arg×HCl, 2.5 mM $CaCl_2$ pH 7.2
11. 20 mM $Na_3$ citrate, 100 mM NaCl, 70 g/l L-Arg×HCl, 2.5 mM $CaCl_2$ pH 6.8
12. 20 mM $Na_3$ citrate, 100 mM NaCl, 60 g/l L-Arg×HCl, 1% L-His, 2.5 mM $CaCl_2$ pH 7.2
13. 20 mM $Na_2$ citrate, 100 mM NaCl, 60 g/l L-Arg×HCl, 2% L-His, 2.5 mM $CaCl_2$ pH 7.2
14. 4 mM $Na_3$ citrate, 100 mM NaCl, 60 g/l L-Arg×HCl, 0.5 mM $CaCl_2$ pH 7.2
15. 20 mM $Na_3$ citrate, 100 mM NaCl, 60 g/l L-Arg×HCl, 30 mM aminobenzoic acid, 2.5 mM $CaCl_2$ pH 7.2
16. 4 mM $Na_3$ citrate, 100 mM NaCl, 60 g/l L-Arg×HCl pH 7.2
17. 4 mM $Na_3$ citrate, 100 mM NaCl, 60 g/l L-Arg×HCl, 2% L-His pH 7.2
18. 4 mM $Na_3$ citrate, 100 mM NaCl, 60 g/l L-Arg×HCl, 2% L-His pH 6.4
19. 4 mM $Na_3$ citrate, 100 mM NaCl, 60 g/l L-Arg×HCl, 2% L-His, 0.5 mM $CaCl_2$ pH 7.2
20. 4 mM $Na_3$ citrate, 100 mM NaCl, 60 g/l L-Arg×HCl, 2.5 mM $CaCl_2$ pH 7.2

The stability of the listed formulations is very good, and a fragment formation is observed to only a very small extent (less than 2% fragments ($\delta$($\leqq$peak 4)) are produced during storage at 30° C. for one month). The solutions are suitable to serve as ingredient of a fibrin glue which can be stored in the liquid state and consists of two or more components.

The invention claimed is:

1. A process for purifying fibrinogen from a fibrinogen solution containing at least one contaminating protein, comprising:
    subjecting the fibrinogen solution to negative chromatography using at least one of a cation exchanger, hydrophobic gel and dye gel, wherein the negative chromatography is performed using either column chromatography or batch chromatography, wherein interaction of the at least one contaminating protein with a stationary phase over which the fibrinogen solution passes is stronger than interaction of fibrinogen with the stationary phase, such that a majority of the fibrinogen is eluted from a column of the column chromatography, or remains in a supernatant of the batch chromatography, at the same time that the at least one contaminating protein is mainly bound to the stationary phase.

2. The process as claimed in claim 1, wherein the functional group of the cation exchanger is a sulfomethyl group, sulfopropyl group, or carboxymethyl group or other suitable negatively charged functional group.

3. The process as claimed in claim 1, wherein the hydrophobic gel comprises alkyl groups as functional groups.

4. The process as claimed in claim 1, wherein the hydrophobic gel comprises phenyl groups or derivatized phenyl groups as functional groups.

5. The process as claimed in claim 3, wherein the hydrophobic gel comprises propyl, butyl, pentyl, hexyl or octyl groups as functional groups.

6. The process as claimed in claim 1, wherein the dye gel is a blue dye gel.

7. The process as claimed in claim 1, wherein the dye gel is a red or green dye gel.

8. The process as claimed in claim 1, wherein the dye gel is at least one of Blue HyperD, Mimetic Blue Agarose, Mimetic Blue SA P6XL, Mimetic Blue 1 P6XL, Blue Trisacryl Plus LS, Blue Uniflow, Blue Sepharose 6FF, Blue Sepharose CL 6B, Red Sepharose CL 6B, Fractogel TSK AF Green and Matrex gel Green A.

9. The process as claimed in claim 1, wherein the negative chromatography is carried out at a pH between 5.5 and 9.

10. The process as claimed in claim 1, wherein the yield of fibrinogen in a flow-through of the column chromatography or in a supernatant of the batch chromatography is $\geqq$50%.

11. The process as claimed in claim 1, wherein the negative chromatography is carried out in the presence of substances which weaken the binding of plasminogen to fibrinogen.

12. The process as claimed in claim 1, wherein the fibrinogen solution comprises at least one of blood, milk from transgenic animals or a fermentation supernatant or a fraction produced therefrom.

13. The process as claimed in claim 12, wherein the fibrinogen solution comprises human plasma, a plasma fraction or cryoprecipitate.

14. The process as claimed in claim 1, further comprising at least one precipitation of fibrinogen.

15. The process as claimed in claim 14, wherein the fibrinogen is precipitated with at least one amino acid.

16. The process as claimed in claim 1, further comprising removing plasminogen on gel material comprising lysine or lysine analogs as the functional group.

17. The process as claimed in claim 1, further comprising inactivation or depletion of infectious particles.

18. The process as claimed in claim 10, wherein the yield of fibrinogen in the flow-through of the negative chromatography is $\geq 70\%$.

19. The process as claimed in claim 15, wherein the at least one amino acid is glycine.

20. A process for purifying fibrinogen from a fibrinogen solution containing at least one contaminating protein, consisting essentially of:
    subjecting the fibrinogen solution to negative chromatography using at least one of a cation exchanger, hydrophobic gel and dye gel, wherein the negative chromatography is performed using either column chromatography or batch chromatography;
    wherein interaction of at least one contaminating protein with a stationary phase is stronger than interaction of fibrinogen with the stationary phase, such that a majority of the fibrinogen is eluted from a column of the column chromatography, or remains in a supernatant of the batch chromatography, at the same time that the at least one contaminating protein is mainly bound to the stationary phase.

21. A process for purifying fibrinogen from a fibrinogen solution containing at least one contaminating protein, comprising:
    subjecting the fibrinogen solution to negative chromatography using at least one of a cation exchanger, hydrophobic gel and dye gel, wherein the negative chromatography is performed using either column chromatography or batch chromatography;
    wherein interaction of at least one contaminating protein with a stationary phase over which the fibrinogen solution passes is stronger than interaction of fibrinogen with the stationary phase, such that fibrinogen is mainly eluted from a column of the column chromatography, or remains in a supernatant of the batch chromatography, at the same time that the at least one contaminating protein is mainly bound to the stationary phase; and
    wherein throughout the process no more than 50% of the fibrinogen is bound within the negative chromatography.

* * * * *